(12) United States Patent
Corti et al.

(10) Patent No.: US 11,446,395 B2
(45) Date of Patent: *Sep. 20, 2022

(54) AAV VECTOR FOR TREATMENT OF FRIEDREICH'S ATAXIA

(71) Applicant: University of Florida Research Foundation, Incorporated, Gainesville, FL (US)

(72) Inventors: Manuela Corti, Alachua, FL (US); Barry John Byrne, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/365,614

(22) Filed: Jul. 1, 2021

(65) Prior Publication Data

US 2021/0330815 A1  Oct. 28, 2021

Related U.S. Application Data

(63) Continuation of application No. 16/745,962, filed on Jan. 17, 2020, which is a continuation of application No. 15/568,961, filed as application No. PCT/US2016/029084 on Apr. 23, 2016, now Pat. No. 10,617,770.

(60) Provisional application No. 62/152,780, filed on Apr. 24, 2015.

(51) Int. Cl.
| | |
|---|---|
| *A61K 48/00* | (2006.01) |
| *C12N 15/86* | (2006.01) |
| *A61K 31/7088* | (2006.01) |
| *C12N 15/864* | (2006.01) |
| *A61P 25/00* | (2006.01) |
| *A61K 9/00* | (2006.01) |

(52) U.S. Cl.
CPC .......... *A61K 48/005* (2013.01); *A61K 9/0019* (2013.01); *A61K 31/7088* (2013.01); *A61P 25/00* (2018.01); *C12N 15/86* (2013.01); *C12N 15/8645* (2013.01); *C12N 2750/14143* (2013.01); *C12N 2800/22* (2013.01); *C12N 2840/105* (2013.01)

(58) Field of Classification Search
CPC .. A61K 48/00; A61K 48/005; A61K 48/0058; A61K 48/0066; A61K 9/0019; A61P 25/00; A61P 25/14; C12N 15/86; C12N 15/8645; C12N 2750/14143; C12N 2800/22

See application file for complete search history.

(56) References Cited

U.S. PATENT DOCUMENTS

| | | | |
|---|---|---|---|
| 9,066,966 B2 | 6/2015 | Puccio et al. | |
| 10,617,770 B2* | 4/2020 | Corti | A61K 48/005 |
| 2007/0161031 A1 | 7/2007 | Trinklein et al. | |
| 2014/0221462 A1* | 8/2014 | Puccio | A61K 9/0019 |
| | | | 514/44 R |
| 2015/0182637 A1 | 7/2015 | Barkats et al. | |
| 2017/0128528 A1* | 5/2017 | Samulski | A61K 38/1709 |
| 2018/0021364 A1* | 1/2018 | Stewart | A61K 48/0075 |
| | | | 435/456 |
| 2020/0138975 A1* | 5/2020 | Corti | C12N 15/86 |
| 2021/0322571 A1 | 10/2021 | Corti et al. | |

FOREIGN PATENT DOCUMENTS

| | | |
|---|---|---|
| WO | WO 2005/080573 A1 | 9/2005 |
| WO | WO 2014/095922 A1 | 6/2014 |

OTHER PUBLICATIONS

GenBank AH003505.2, *Homo sapiens* frataxin gene, complete cds, alternatively spliced (2016).*
GenBank NM_000144.5, *Homo sapiens* frataxi, transcript variant 1, mRNA (2021).*
GenBank BC023633, *Homo sapiens* frataxin, mRNA, complete cds (2006).*
GenBank BC048097.1, *Homo sapiens* frataxin, mRNA, complete cds (2006).*
GenBank HSU43747, Human frataxin mRNA, complete cds (1996).*
GenBank NM_00161706.1, *Homo sapiens* frataxin, transcript variant 3, mRNA (2009).*
Tsai et al (Biochemistry 49: 9132-9139, 2010).*
Meyer-Luehmann et al, J. Neurosci. 29(4): 12636-12640, 2009.*
Muenzer et al, Mol. Ther. 16(Suppl 1): S45, 2008.*
Bandiera et al, PLoS One 8(1): e54791, 7 pages, 2013.*
Athanasopoulos et al, Gene Therapy 11: S109-121, 2004.*
U.S. Appl. No. 16/745,962, filed Jan. 17, 2020, Corti et al.
U.S. Appl. No. 17/365,845, filed Jul. 1, 2021, Corti et al.
EP 16784053.7, Sep. 17, 2018, Extended European Search Report.
PCT/US2016/029084, Aug. 4, 2016, International Search Report and Written Opinion.
PCT/US2016/029084, Nov. 2, 2017, International Preliminary Report on Patentability.
Extended European Search Report for Application No. EP 16784053.7 dated Sep. 17, 2018.
International Search Report and Written Opinion for Application No. PCT/US2016/029084 dated Aug. 4, 2016.

(Continued)

*Primary Examiner* — Kevin K Hill
(74) *Attorney, Agent, or Firm* — Wolf, Greenfield & Sacks, P.C.

(57) ABSTRACT

Provided herein are nucleic acids, recombinant adeno-associated viral particles, compositions and methods related to treating Friedreich's ataxia. In some examples, the nucleic acids, recombinant adeno-associated viral particles, compositions and methods involve us of a FXN coding sequence, a truncated FXN 3' UTR, and a prompter.

22 Claims, 5 Drawing Sheets

Specification includes a Sequence Listing.

(56) References Cited

OTHER PUBLICATIONS

International Preliminary Report on Patentability for Application No. PCT/US2016/029084 dated Nov. 2, 2017.

Campuzano et al., *Homo sapiens* chromosome 9 frataxin (FRDA) gene, complete cds, alternatively spliced. GenBank Acc. No. AH003505. 2. Jun. 10, 2016. Accessible at https://www.ncbi.nlm.nih.gov/nuccore/AH003505.2/. 3 pages.

Gérard et al., An AAV9 coding for frataxin clearly improved the symptoms and prolonged the life of Friedreich ataxia mouse models. Mol Ther Methods Clin Dev. Oct. 8, 2014;1:14044. doi: 10.1038/mtm.2014.44. eCollection 2014.

Muenzer et al., Long-Term Somatic and CNS Correction in MPS II Mice after Combined INtravenous and Intrathecal Administration of a Self-Complementary AAV2 Vector. Mol. Ther. 2008;16(Suppl 1):S45. 1 page.

Pacak et al., Tissue specific promoters improve specificity of AAV9 mediated transgene expression following intra-vascular gene delivery in neonatal mice. Genet Vaccines Ther. Sep. 23, 2008;6:13. doi: 10.1186/1479-0556-6-13.

Perdomini et al., Prevention and reversal of severe mitochondrial cardiomyopathy by gene therapy in a mouse model of Friedreich's ataxia. Nat Med. May 2014;20(5):542-7. doi: 10.1038/nm.3510. Epub Apr. 6, 2014.

Samaranch et al., Adeno-associated virus serotype 9 transduction in the central nervous system of nonhuman primates. Hum Gene Ther. Apr. 2012;23(4):382-9. doi: 10.1089/hum.2011.200. Epub Mar. 28, 2012.

Schuster et al., Biodistribution of adeno-associated virus serotype 9 (AAV9) vector after intrathecal and intravenous delivery in mouse. Front Neuroanat. Jun. 10, 2014;8:42. doi: 10.3389/fnana.2014.00042.

Wardle et al., *Homo sapiens* frataxin (FXN), transcript variant 3, mRNA. NCBI Ref Sequence: NM_001161706.1. Jun. 11, 2009. Accessible at https://www.ncbi.nlm.nih.gov/nuccore/NM_001161706.1?report=genbank. 3 pages.

* cited by examiner

AAV VECTOR FOR TREATMENT OF FRIEDREICH'S ATAXIA

RELATED APPLICATIONS

This Application is a Continuation of U.S. application Ser. No. 16/745,962, filed Jan. 17, 2020, entitled "AAV VECTOR FOR TREATMENT OF FRIEDREICH'S ATAXIA", which is a Continuation of U.S. application Ser. No. 15/568,961, filed Oct. 24, 2017, entitled "AAV VECTOR FOR TREATMENT OF FRIEDREICH'S ATAXIA", which is a national stage filing under 35 U.S.C. 371 of International Patent Application Serial No. PCT/US2016/029084, filed Apr. 23, 2016, entitled "AAV VECTOR FOR TREATMENT OF FRIEDREICH'S ATAXIA", which claims priority under 35 U.S.C. § 119(e) to U.S. Provisional Application Ser. No. 62/152,780, entitled "AAV VECTOR FOR TREATMENT OF FRIEDREICH'S ATAXIA" filed Apr. 24, 2015, each of which is herein incorporated by reference in its entirety.

BACKGROUND

Friedreich's ataxia is a genetic disease that causes damage to the nervous system, resulting in degeneration of the spinal cord and peripheral nerves. Friedreich's ataxia is caused by a mutation in the FXN gene that results in an expansion of an intronic GAA repeat, which leads to reduced expression of the mitochondrial protein frataxin. There is currently no approved cure for Friedreich's ataxia.

SUMMARY

Aspects of the disclosure relate to nucleic acids, recombinant adeno-associated virus (rAAV) particles, compositions, and methods related to gene therapy for Friedreich's ataxia (FRDA).

As described herein, a rAAV nucleic acid vector was designed containing a codon-optimized human FXN gene with a truncated human FXN 3' UTR, operably linked to a promoter. When this vector was delivered in a rAAV particle to cardiomyocytes differentiated from induced pluripotent stem cells (IPSC) derived from FRDA, the cells had increased mitochondrial activity. This improvement in mitochondrial activity was correlated with increased levels of FXN expression in vitro. It is believed that this vector may be useful for treatment of FRDA.

In some aspects, the disclosure provides a nucleic acid comprising an expression construct comprising a human frataxin (FXN) coding sequence and a truncated human FXN 3' untranslated region (UTR) operably linked to a promoter (e.g., a Desmin promoter, a CBA promoter, a hFXNPro, or other suitable promoter), wherein the expression construct is flanked on each side by an inverted terminal repeat sequence (e.g., an AAV ITR).

In some embodiments, the human FXN coding sequence is codon-optimized for expression in human cells. In some embodiments, the FXN coding sequence comprises the sequence of SEQ ID NO: 1. In some embodiments, the promoter comprises one or more of the following: a Desmin promoter, a chicken β-actin (CBA) promoter, or an endogenous human FXN promoter (hFXNPro), or a fragment or derivative of one or more thereof sufficient to drive expression of the FXN coding sequence (e.g., in human cells). In some embodiments, the Desmin promoter comprises the sequence of SEQ ID NO: 2. In some Zo embodiments, the CBA promoter comprises the sequence of SEQ ID NO: 7. In some embodiments, the hFXNPro comprises the sequence of SEQ ID NO: 8. In some embodiments, the truncated human FXN 3' UTR has the sequence of SEQ ID NO: 3. In some embodiments, the expression construct comprises the sequence of SEQ ID NO: 4 (or a portion thereof comprising a gene of interest under the control of a promoter of interest, optionally flanked by ITR sequences). In some embodiments, the nucleic acid is a recombinant adeno-associated virus (rAAV) vector. In some embodiments, the nucleic acid is a single-stranded or self-complementary rAAV nucleic acid vector.

Other aspects of the disclosure relate to a recombinant adeno-associated virus (rAAV) particle comprising a nucleic acid as described herein. In some embodiments, the nucleic acid comprises an expression construct comprising a human frataxin (FXN) coding sequence and a truncated human FXN 3' untranslated region (UTR) operably linked to a promoter (e.g., a Desmin promoter, a CBA promoter, a hFXNPro, or other suitable promoter), wherein the expression construct is flanked on each side by an inverted terminal repeat sequence.

In some embodiments, the human FXN coding sequence is codon-optimized for expression in human cells. In some embodiments, the FXN coding sequence comprises the sequence of SEQ ID NO: 1. In some embodiments, the promoter comprises one or more of the following: a Desmin promoter, a chicken β-actin (CBA) promoter, or an endogenous human FXN promoter (hFXNPro), or a fragment or derivative of one or more thereof sufficient to drive expression of the FXN coding sequence (e.g., in human cells). In some embodiments, the Desmin promoter comprises the sequence of SEQ ID NO: 2. In some embodiments, the CBA promoter comprises the sequence of SEQ ID NO: 7. In some embodiments, the hFXNPro comprises the sequence of SEQ ID NO: 8. In some embodiments, the truncated human FXN 3' UTR has the sequence of SEQ ID NO: 3. In some embodiments, the expression construct comprises the sequence of SEQ ID NO: 4 (or a portion thereof comprising a gene of interest under the control of a promoter of interest, optionally flanked by ITR sequences). In some embodiments, the nucleic acid is a recombinant adeno-associated virus (rAAV) vector. In some embodiments, the nucleic acid is a single-stranded or self-complementary rAAV nucleic acid vector.

In some embodiments, the rAAV particle is an AAV9 particle.

In yet other aspects, the disclosure relates to a composition comprising a plurality of an rAAV particle as described herein. In some embodiments, the rAAV particle comprises a nucleic acid as described herein.

In some embodiments, the human FXN coding sequence is codon-optimized for expression in human cells. In some embodiments, the FXN coding sequence comprises the sequence of SEQ ID NO: 1. In some embodiments, the promoter comprises one or more of the following: a Desmin promoter, a chicken β-actin (CBA) promoter, or an endogenous human FXN promoter (hFXNPro), or a fragment or derivative of one or more thereof sufficient to drive expression of the FXN coding sequence (e.g., in human cells). In some embodiments, the Desmin promoter comprises the sequence of SEQ ID NO: 2. In some embodiments, the CBA promoter comprises the sequence of SEQ ID NO: 7. In some embodiments, the hFXNPro comprises the sequence of SEQ ID NO: 8. In some embodiments, the truncated human FXN 3' UTR has the sequence of SEQ ID NO: 3. In some embodiments, the expression construct comprises the sequence of SEQ ID NO: 4 (or a portion thereof comprising a gene of interest under the control of a promoter of interest, optionally flanked by ITR sequences). In some embodiments, the nucleic acid is a recombinant adeno-associated virus (rAAV) vector. In some embodiments, the nucleic acid is a single-stranded or self-complementary rAAV nucleic acid vector.

In some embodiments, the rAAV particle is an AAV9 particle (e.g., the rAAV particle comprises viral capsid proteins of serotype 9).

In some embodiments, the composition further comprises a pharmaceutically acceptable carrier.

In other aspects, the disclosure provides a method of treating Friedreich's ataxia, the method comprising administering a therapeutically effective amount of an rAAV particle as described above or as described elsewhere herein or a composition as described above or as described elsewhere herein to a subject having Friedreich's ataxia. In some embodiments, the rAAV particle or composition are administered via intravenous injection. In some embodiments, the rAAV particle or composition are administered via intrathecal injection. In some embodiments, the rAAV particle or composition are administered via intracisternal injection. In some embodiments, the rAAV particle or composition are administered via intravenous injection and intrathecal injection. In some embodiments, the rAAV particle or composition are administered via intravenous injection and intracisternal injection.

In some embodiments, the ratio of rAAV particle administered to the subject via intravenous injection to rAAV particle administered to the subject via intrathecal injection is between 10:1 and 1:1 (e.g., around 5:1, or around 10:1). In some embodiments, the ratio of rAAV particle administered to the subject via intravenous injection to rAAV particle administered to the subject via intrathecal injection is between 1:1 and 1:10 (e.g., around 1:5, or around 1:10). In some embodiments, the ratio of rAAV particle administered to the subject via intravenous injection to rAAV particle administered to the subject via intracisternal injection is between 10:1 and 1:1 (e.g., around 5:1, or around 10:1). In some embodiments, the ratio of rAAV particle administered to the subject via intravenous injection to rAAV particle administered to the subject via intracisternal injection is between 1:1 and 1:10 (e.g., around 1:5, or around 1:10).

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION

Figure 1:
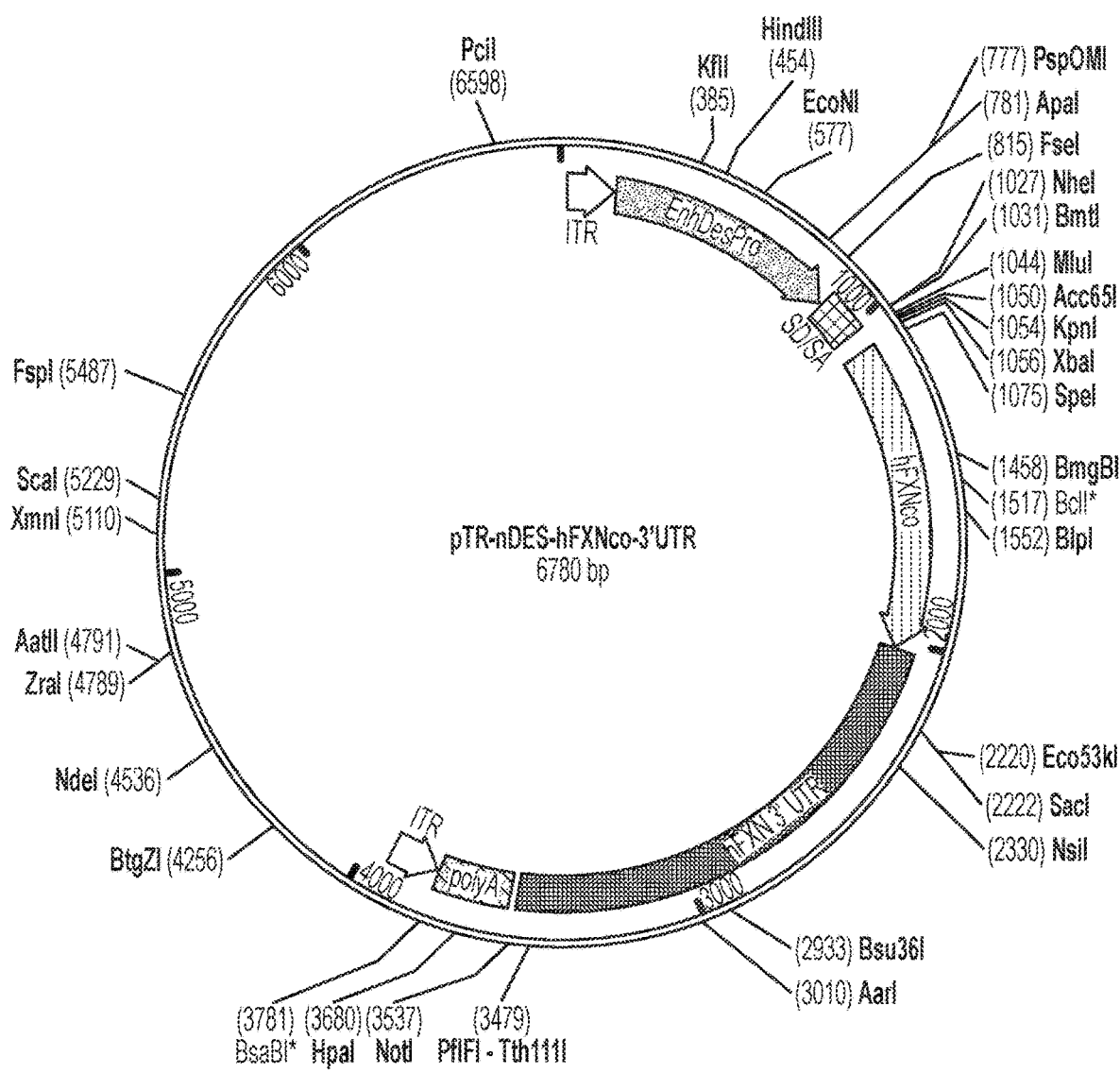
FIG. 1 is a non-limiting plasmid map showing an expression construct containing a Desmin (DES) promoter, a codon-optimized human FXN coding sequence, and a truncated human FXN 3' UTR, the expression construct flanked by inverted terminal repeat sequences (ITRs).

Friedrich's ataxia (FRDA) is an autosomal recessive disorder caused by a trinucleotide repeat expansion (TNR) of the frataxin (FXN) gene, on chromosome 9q12-13, which leads to a deficiency in the mitochondrial protein frataxin (FXN). FRDA affects 1 in 50,000 people worldwide and is characterized by progressive neural degeneration, such as ataxia, sensory loss, muscle weakness, and hypertrophic cardiomyopathy. Symptoms generally present at puberty and patients have a shorter than normal life expectancy reaching 40-50 years of age.

Frataxin is a highly conserved, 210 amino acid (~17 kDa) protein encoded in the nucleus. While frataxin's specific function remains unclear, homozygous deletions are embryonically lethal. Evidence suggests frataxin is involved in iron metabolism, iron storage, iron-sulfur cluster (ISC) formation, and protection against reactive oxygen species (ROS). Dysregulation of FXN leads to iron accumulation in the mitochondria and insufficient iron in the cytoplasm. Excess mitochondrial iron increases the incidence of iron-catalyzed reduction of hydrogen peroxide generating toxic ROS. The increase in ROS disrupts iron homeostasis in the mitochondria and affects the ISC aconitase, a major component of cellular respiration.

Currently patients with FRDA receive palliative care as there is no FDA approved treatment.

The major neurological symptoms of FRDA include muscle weakness and ataxia, a loss of balance and coordination. FRDA mostly affects the spinal cord and the peripheral nerves that connect the spinal cord to the body's muscles and sensory organs. FRDA affects the function of the cerebellum and also the musculature of the heart. There is a high prevalence of diabetes in FRDA patients as well. FXN deficiency in pancreatic islet cells causes diabetes (Ristow, M, et al., J Clin Invest. 112(4): 527-534, 2003).

In some embodiments, the neurological degeneration in FRDA patients needs to be addressed. In some embodiments, the cardiac disease in FRDA patients needs to be addressed. In some embodiments, there is a need for strategies to treat the systemic manifestations of the disease, which may include disease in the heart, CNS and/or pancreatic islet cells.

Over the past decade the field of gene therapy for the treatment of genetic diseases has made a resurgence including marketing authorization for an AAV product in the EU. In some embodiments, the fundamental principle is based on the ability to restore proper gene function in target tissues.

Herein are disclosed nucleic acids, compositions and methods that can be used to achieve global gene transfer using AAV vectors, and that can target both the neurological and cardiac impairment in FRDA. Herein, "global" refers to an entire organ, system of the body (e.g., CNS) or body. The disclosed nucleic acids encoding FXN, compositions and methods, which relate to both choice of promoter and routes of rAAV particle delivery to a subject, enable targeting multiple affected organs in a subject with FRDA, including cardiac muscle, pancreas (e.g., pancreatic islet cells), and/or CNS (e.g., dorsal root ganglia, and the cerebellum).

According to the disclosure, a gene therapy strategy that increases frataxin levels may be useful to treat FRDA or one or more symptoms thereof.

Adeno-associated viruses (AAVs) are among the most common vectors used in gene therapy due to persistent, robust gene expression, a lack of toxicity, and limited immune response. However, challenges in AAV-mediated neural delivery and targeting have yet to be fully characterized.

As described herein, a rAAV-FXN vector driven by a promoter sequence (e.g., a Desmin promoter) was developed and shown to be capable of increasing expression of frataxin and restoring mitochondrial function in cells from FRDA patients.

Recombinant Adeno-Associated Virus (rAAV) Particles and Nucleic Acids

Aspects of the disclosure relate to recombinant AAV (rAAV) particles and nucleic acids. In some embodiments, a nucleic acid is provided, the nucleic acid comprising an expression construct containing a FXN coding sequence (e.g., a human FXN coding sequence) linked to a promoter (e.g., a Desmin promoter, for example a human Desmin promoter, a CBA promoter, a hFXNPro, or other suitable promoter). In some embodiments, the expression construct further contains a FXN 3' untranslated region (UTR) that is 3' to the FXN coding sequence. In some embodiments, the expression construct is flanked on each side by an inverted terminal repeat sequence (e.g., an AAV ITR).

Recombinant AAV (rAAV) nucleic acids are, herein, equivalent to rAAV nucleic acid vectors (e.g., a plasmid that is used to prepare a rAAV, a nucleic acid comprising a gene of interest and a promoter flanked by ITRs that are packaged in an rAAV particle, or other nucleic acid described herein that comprises or encodes a nucleic acid that is packaged in a rAAV, or that encodes one or more viral proteins). Accordingly, rAAV nucleic acids can be circular, linear, single-stranded, or double-stranded, depending on the context. In some embodiments, a nucleic acid is an RNA molecule. In some embodiments, a nucleic acid is a DNA molecule. In some embodiments, recombinant AAV (rAAV) vectors can be nucleic acid vectors that are used to transfect cells in which the expression construct that is comprised by the vector is packaged (or encapsidated) into rAAV particles. In some embodiments, rAAV vectors can be the nucleic acid flanked by ITRs (and including the ITRs) that is packaged in a rAAV.

It should be appreciated that a composition or nucleic acid described herein with reference to a particular sequence (e.g., with reference to a particular SEQ ID NO:) can be provided as a composition or nucleic acid (e.g., RNA or DNA) comprising a single-stranded nucleic acid having that sequence, or a composition or nucleic acid (e.g., RNA or DNA) comprising a single-stranded nucleic acid having the complement of that sequence, or a composition or nucleic acid (e.g., RNA or DNA) comprising a double-stranded nucleic acid one strand of which has that sequence, or a composition or nucleic acid (e.g., RNA or DNA) comprising a portion of one or more of such nucleic acids, or a combination thereof.

In some embodiments, the FXN coding sequence encodes a human frataxin protein. An exemplary human frataxin protein is shown below:

Exemplary Human FXN Protein (SEQ ID NO: 6)
MWTLGRRAVAGLLASPSPAQAQTLTRVPRPAELAPLCGRRGLRTDIDATC

TPRRASSNQRGLNQIWNVKKQSVYLMNLRKSGTLGHPGSLDETTYERLAE

ETLDSLAEFFEDLADKPYTFEDYDVSFGSGVLTVKLGGDLGTYVINKQTP

NKQIWLSSPSSGPKRYDWTGKNWVFSHDGVSLHELLAAELTKALKTKLDL

SWLAYSGKDAIDIPSPVLRTLKAIRPRPQLHYAAEVCFLLLLLFIFFIPA

FEDSWAMCHSSVERMCCLLPCPQVLIFNFYGRFFGLSDFLPHMIPLIFYN

VLCLYLNITTFKKAK

In some embodiments, the FXN coding sequence is codon-optimized for expression in human cells, e.g., by adjusting codon usage within the coding sequence to codons commonly used by human cells. In some embodiments, the FXN coding sequence is further optimized to remove extra GC content, ribosomal binding sites, consensus and cryptic splice sites, repeats, and/or secondary structures. Optimization of coding sequences (e.g., codon-optimization) can be accomplished using any method known in the art, e.g., using GeneOptimizer® software from LifeTechnologies. In some embodiments, the codon-optimized human FXN coding sequence is at least 80%, 85%, 90%, 95%, 96%, 97%, 98%, 99%. 100% identical to the sequence of SEQ ID NO: 1. In some embodiments, the codon-optimized human FXN coding sequence comprises the sequence of SEQ ID NO: 1.

Exemplary codon-optimized human FXN coding sequence (SEQ ID NO: 1)
ATGTGGACACTGGGGAGAAGGGCCGTGGCTGGACTGCTGGCTTCTCCATC

TCCAGCCCAGGCCCAGACCCTGACCAGAGTGCCTAGACCTGCCGAACTGG

CCCCTCTGTGTGGCAGAAGAGGCCTGAGAACCGACATCGACGCCACCTGT

ACCCCCAGAAGGGCCAGCAGCAATCAGCGGGGCCTGAATCAGATCTGGAA

CGTGAAGAAACAGAGCGTGTACCTGATGAACCTGAGAAAGAGCGGCACCC

TGGGCCACCCTGGAAGCCTGGATGAGACAACCTACGAGCGGCTGGCCGAG

GAAACCCTGGATTCCCTGGCCGAGTTCTTCGAGGACCTGGCCGACAAGCC

CTACACCTTCGAGGATTACGACGTGTCCTTCGGCAGCGGCGTGCTGACAG

TGAAGCTGGGCGGAGATCTGGGCACCTACGTGATCAACAAGCAGACCCCC

AACAAACAGATCTGGCTGAGCAGCCCCAGCAGCGGCCCCAAGAGATACGA

TTGGACCGGCAAGAACTGGGTGTTCAGCCACGACGGCGTGTCCCTGCATG

-continued
```
AGCTGCTGGCTGCCGAGCTGACCAAGGCCCTGAAAACAAAGCTGGACCTG

AGCTGGCTGGCCTACAGCGGCAAAGATGCCATCGATATCCCCAGCCCCGT

TTTAAGGACATTAAAAGCTATCAGGCCAAGACCCCAGCTTCATTATGCAG

CTGAGGTCTGTTTTTTGTTGTTGTTGTTGTTTATTTTTTTATTCCTGCT

TTTGAGGACAGTTGGGCTATGTGTCACAGCTCTGTAGAAAGAATGTGTTG

CCTCCTACCTTGCCCCCAAGTTCTGATTTTTAATTTCTATGGAAGATTTT

TTGGATTGTCGGATTTCCTCCCTCACATGATACCCCTTATCTTTTATAAT

GTCTTATGCCTATACCTGAATATAACAACCTTTAAAAAAGCAAAATAA
```

In some embodiments, the promoter is a Desmin promoter, or a fragment or variant thereof that has at least 80%, 85%, 90%, 95%, 96%, 97%, 98%, 99%, 100%, or more of the activity (e.g., promotion of transcription of a gene, such as in a neuronal or muscle cell) of a wild-type human Desmin promoter. In some embodiments, the promoter comprises two or more fragments of a Desmin promoter (e.g., an enhancer fragment and a basal promoter fragment, which may be fused together optionally with a spacer sequence). The fragment(s) may be 10, 20, 30, 40, 50, 60, 70, 80, 90, 100, 120, 150, 200, 250, 500, 1000 or more nucleotides shorter than a wild-type human Desmin promoter. In some embodiments, the Desmin promoter comprises one or more of (e.g., one, two, three, or four of) a MEF2 responsive element, a MyoD E-box, a CACC box and a TATA box. In some embodiments, the promoter has a sequence that is at least 80%, 85%, 90%, 95%, 96%, 97%, 98%, 99%, 100% identical to the sequence of SEQ ID NO: 2. In some embodiments, the promoter is a Desmin promoter having the sequence of SEQ ID NO: 2.

Exemplary Desmin Promoter Sequence (Potential MEF2 Responsive Element (with 9 bp AT-Rick Core) at Position 65-73, MyoD E-Box at Position 97-102, CACC Box at Position 160-163 (Binds Nuclear Factors Present in Cardiac and Skeletal Muscle Myocytes), CACC Box at Position 176-179, CACC Box at Position 179-182, CACC Box at Position 253-256, MyoD E-Box at Position 270-275, CACC Box at Position 338-341, MyoD E-Box at Position 542-547, TATA Box at Position 585-590, and CACC Box at Position 696-699).

```
                                        (SEQ ID NO: 2)
GATCTTACCCCTGCCCCCCACAGCTCCTCTCCTGTGCCTTGTTTCCCAG

CCATGCGTTCTCCTCTATAAATACCCGCTCTGGTATTTGGGGTTGGCAGC

TGTTGCTGCCAGGGAGATGGTTGGGTTGACATGCGGCTCCTGACAAAACA

CAAACCCCTGGTGTGTGTGGGCGTGGGTGGTGTGAGTAGGGGATGAATC

AGGGAGGGGCGGGGGACCCAGGGGGCAGGAGCCACACAAAGTCTGTGCG

GGGGTGGGAGCGCACATAGCAATTGGAAACTGAAAGCTTATCAGACCCTT

TCTGGAAATCAGCCCACTGTTTATAAACTTGAGGCCCCACCCTCGAGATA

ACCAGGGCTGAAAGAGGCCCGCCTGGGGGCTGGAGACATGCTTGCTGCCT

GCCCTGGCGAAGGATTGGCAGGCTTGCCCGTCACAGGACCCCCGCTGGCT

GACTCAGGGGCGCAGGCCTCTTGCGGGGGAGCTGGCCTCCCCGCCCCCAC

GGCCACGGGCCGCCCTTTCCTGGCAGGACAGCGGGATCTTGCAGCTGTCA

GGGGAGGGGAGGCGGGGGCTGATGTCAGGACGCATACAAATAGTGCCGAC
```

-continued
```
GGCTGGGGGCCCTGTCTCCCCTCGCCGCATCCACTCTCCGGCCGGCCGCC

TGTCCGCCGCCTCCTCCGTGCGCCCGCCAGCCTCGCCCGCGCCGTCACCG

TGAGGCACTGGG
```

In some embodiments, the promoter is a Chicken β-actin (CBA) promoter, or a fragment or variant thereof that has at least 80%, 85%, 90%, 95%, 96%, 97%, 98%, 99%, 100%, or more of the activity (e.g., promotion of transcription of a gene, such as in a neuronal or muscle cell) of a wild-type full-length promoter. In some embodiments, the promoter comprises two or more fragments of a CBA promoter (e.g., an enhancer fragment and a basal promoter fragment, which may be fused together optionally with a spacer sequence). The fragment(s) may be 10, 20, 30, 40, 50, 60, 70, 80, 90, 100, 120, 150, 200, 250, 500, 1000 or more nucleotides shorter than the full-length CBA promoter. In some embodiments, the CBA promoter comprises one or more of (e.g., one, two, three, or four of) a MEF2 responsive element, a MyoD E-box, a CACC box and a TATA box. In some embodiments, the promoter has a sequence that is at least 80%, 85%, 90%, 95%, 96%, 97%, 98%, 99%, 100% identical to the sequence of SEQ ID NO: 7. In some embodiments, the promoter is a CBA promoter having the sequence of SEQ ID NO: 7.

```
Exemplary CBA promoter sequence
                                        (SEQ ID NO: 7)
ctagatctgaattcggtaccctagttattaatagtaatcaattacgg ggtcattagttcatagcccatatatggagttccgcgttacataactt acggtaaatggcccgcctggctgaccgcccaacgaccccgcccatt gacgtcaataatgacgtatgttcccatagtaacgccaatagggactt tccattgacgtcaatgggtggactatttacggtaaactgcccacttg gcagtacatcaagtgtatcatatgccaagtacgccccctattgacgt caatgacggtaaatggcccgcctggcattatgcccagtacatgacct tatgggactttcctacttggcagtacatctacgtattagtcatcgct attaccatggtcgaggtgagccccacgttctgcttcactctcccat ctccccccctccccaccccaattt g[a][a][a][a][a][a]

[a][a][a][g]gcagcga[ggggggcgggggggggggggggggc gcgcgcca ggcggggcggggcggggcgaggggcggggcggggcgaggcggagagg tgcggcggcagccaatcagagcggcgcgctccgaaagtttccttta tggcgaggcggcggcggcggcggccctataaaagcgaagcgcgcgg cgggcgggagtcgctgcgacgctgccttcgcccgtgccccgctccg ccgccgctcgcgccgcccgccccggctctgactgaccgcgttactc ccacaggtgagcgggcgggacggcccttctcctccgggctgtaatta gcgcttggtttaatgacggcttgttt[a][a][a]

[a][a]ggc[a]gc[a]gaaa gcc[a]gagggg[a]ccgggagggcc[a][a]

g[a]gcggggggagcggc[a]
```

-continued

```
gggggggcgtgcgtgtgtgtgcgtggggagcgccgcgtgcggcc cgcgctgcccgcggctgtgagcgctgcgggcgcggcgcggggcttt gtgcgctccgcagtgtgcgcgaggggagcgcggccggggcggtgcc ccgcggtgcggggggggctgcgaggggaacaaaggctgcgtgcgggg tgtgtgcgtggggggtgagcagggggtgtgggcgcggcggtcgggc tgtaaccccccctgcaccccctccccgagttgctgagcacggccc ggcttcgggtgcggggctccgtacggggcgtggcgcggggctcgccg tgccgggcgggggtggcggcaggtggggtgccgggcggggcgggg ccgcctcgggccggggagggctcgggggaggggcgcggcggccccg gagcgccggcggctgtcgaggcgcggcgagccgcagccattgcctt tatggtaatcgtgcgagagggcgcagggacttcctttgtcccaaatc tgtgcggagccgaaatctgggaggcgccgccgcaccccctctagcgg gcgcggggcgaagcggtgcggcgccggcaggaaggaaatgggcgggg agggccttcgtgcgtcgccgcgccgccgtcccttctccctctccag cctcggggctgtccgcggggggacggctgccttcgggggggacgggg cagggcggggttcggcttctggcgtgtgaccggcggctctagagcct ctgctaaccagtgttcatgcctt cttcttttcctacagctcctgggc aacgtgctggttattgtgctgtctcatcattt ggcaaagaattcctcgaagatccgaaggggttcaagcttaaaaa
```

In some embodiments, the promoter is a human FXN promoter (hFXNPro promoter), or a fragment or variant thereof that has at least 80%, 85%, 90%, 95%, 96%, 97%, 98%, 99%, 100%, or more of the activity (e.g., promotion of transcription of a gene, such as in a neuronal or muscle cell) of a wild-type hFXNPro. In some embodiments, the promoter comprises two or more fragments of a hFXNPro (e.g., an enhancer fragment and a basal promoter fragment, which may be fused together optionally with a spacer sequence). The fragment(s) may be 10, 20, 30, 40, 50, 60, 70, 80, 90, 100, 120, 150, 200, 250, 500, 1000 or more nucleotides shorter than a wild-type hFXNPro. In some embodiments, the hFXNPro comprises one or more of (e.g., one, two, three, or four of) a MEF2 responsive element, a MyoD E-box, a CACC box and a TATA box. In some embodiments, the promoter has a sequence that is at least 80%, 85%, 90%, 95%, 96%, 97%, 98%, 99%, 100% identical to the sequence of SEQ ID NO: 8. In some embodiments, the promoter is a hFXNPro having the sequence of SEQ ID NO: 8.

```
Exemplary hFXNPro sequence
                                    (SEQ ID NO: 8)
AAGAAAACTTTCACAATTTGCATCCCTTTGTAATATGTAACAGAAA

TAAAATTCTCTTTTAAAATCTATCAACAATAGGCAAGGCACGGTGG

CTCACGCCTGTCGTCTCAGCACTTTGTGAGGCCCAGGCGGGCAGAT

CGTTTGAGCCTAGAAGTTCAAGACCACCCTGGGCAACATAGCGAAA

CCCCCTTTCTACAAAAAATACAAAAACTAGCTGGGTGTGGTGGTGC

ACACCTGTAGTCCCAGCTACTTGGAAGGCTGAAATGGGAAGACTGC

TTGAGCCCGGGAGGGAGAAGTTGCAGTAAGCCAGGACCACACCACT

GCACTCCAGCCTGGGCAACAGAGTGAGACTCTGTCTCAAACAAACA

AATAAATGAGGCGGGTGGATCACGAGGTCAGTAGATCGAGACCATC

CTGGCTAACACGGTGAAACCCGTCTCTACTAAAAAAAAAAAAAAAT

ACAAAAAATTAGCCAGGCATGGTGGCGGGCGCCTGTAGTCCCAGTT

ACTCGGGAGGCTGAGGCAGGAGAATGGCGTGAAACCGGGAGGCAGA

GCTTGCAGTGAGCCGAGATCGCACCACTGCCCTCCAGCCTGGGCGA

CAGAGCGAGACTCCGTCTCAATCAATCAATCAATCAATAAAATCTA

TTAACAATATTTATTGTGCACTTAACAGGAACATGCCCTGTCCAAA

AAAAACTTTACAGGGCTTAACTCATTTTATCCTTACCACAATCCTA

TGAAGTAGGAACTTTTATAAAACGCATTTTATAAACAAGGCACAGA

GAGGTTAATTAACTTGCCCTCTGGTCACACAGCTAGGAAGTGGGCA

GAGTACAGATTTACACAAGGCATCCGTCTCCTGGCCCCACATACCC

AACTGCTGTAAACCCATACCGGCGGCCAAGCAGCCTCAATTTGTGC

ATGCACCCACTTCCCAGCAAGACAGCAGCTCCCAAGTTCCTCCTGT

TTAGAATTTTAGAAGCGGCGGGCCACCAGGCTGCagtctcccttgg gtcaggggtagtgctaagctgggaagttcttcctgaggtctaacct ctagctgctcccccacagaagaggccgcggccaggggccaccag gggcgccgcagcacccagcgcggagggcggagcgggcggcagac ccggagcagc
```

In some embodiments, the promoter has a sequence that is at least 80%, 85%, 90%, 95%, 96%, 97%, 98%, 99%, 100% identical to the sequence identified as nucleotides 2312-2404 of GenBank accession No. NC_001510.1.

In some embodiments, the FXN 3' untranslated region (UTR) is a truncated FXN 3' UTR. In some embodiments, the truncated FXN 3' UTR is a truncated human FXN 3' UTR. In some embodiments, the truncated FXN 3' UTR is at least 100, 200, 300, 400, 500, 600, 700, 800, 900, 1000, 1500, 2000 or more nucleotides shorter than a wild-type FXN 3' UTR. In some embodiments, the 3' UTR is truncated (e.g., by at least 100, 200, 300, 400, 500, 600, 700, 800, 900, 1000, 1500, 2000 or more nucleotides) and the truncated sequence has at least 85%, 90%, 91%, 92%, 93%, 94%, 95%, 96%, 97%, 98%, or 99% sequence identity with the corresponding sequence in a wild-type FXN 3' UTR. In some embodiments, the 3' UTR is truncated relative to the below wild-type FXN 3' UTR. In some embodiments, the truncated 3' UTR is no more than 2000, 1900, 1800, 1700, 1600, 1500, 1400, 1300, 1200, 1100, or 1000 nucleotides in length.

Exemplary human FXN 3' UTR (SEQ ID NO: 9)

```
   1 ACTAGTGCCA CCATGTGGAC ACTGGGGAGA AGGGCCGTGG CTGGACTGCT GGCTTCTCCA
  61 TCTCCAGCCC AGGCCCAGAC CCTGACCAGA GTGCCTAGAC CTGCCGAACT GGCCCCTCTG
 121 TGTGGCAGAA GAGGCCTGAG AACCGACATC GACGCCACCT GTACCCCCAG AAGGGCCAGC
 181 AGCAATCAGC GGGGCCTGAA TCAGATCTGG AACGTGAAGA AACAGAGCGT GTACCTGATG
 241 AACCTGAGAA AGAGCGGCAC CCTGGGCCAC CCTGGAAGCC TGGATGAGAC AACCTACGAG
 301 CGGCTGGCCG AGGAAACCCT GGATTCCCTG GCCGAGTTCT TCGAGGACCT GGCCGACAAG
 361 CCCTACACCT TCGAGGATTA CGACGTGTCC TTCGGCAGCG GCGTGCTGAC AGTGAAGCTG
 421 GGCGGAGATC TGGGCACCTA CGTGATCAAC AAGCAGACCC CAACAAACA GATCTGGCTG
 481 AGCAGCCCCA GCAGCGGCCC CAAGAGATAC GATTGGACCG GCAAGAACTG GGTGTTCAGC
 541 CACGACGGCG TGTCCCTGCA TGAGCTGCTG GCTGCCGAGC TGACCAAGGC CCTGAAAACA
 601 AAGCTGGACC TGAGCTGGCT GGCCTACAGC GGCAAAGATG CCATCGATAT CCCCAGCCCC
 661 GTTTTAAGGA CATTAAAAGC TATCAGGCCA AGACCCCAGC TTCATTATGC AGCTGAGGTC
 721 TGTTTTTTGT TGTTGTTGTT GTTTATTTTT TTTATTCCTG CTTTTGAGGA CAGTTGGGCT
 781 ATGTGTCACA GCTCTGTAGA AAGAATGTGT TGCCTCCTAC CTTGCCCCCA AGTTCTGATT
 841 TTTAATTTCT ATGGAAGATT TTTTGGATTG TCGGATTTCC TCCCTCACAT GATACCCCTT
 901 ATCTTTTATA ATGTCTTATG CCTATACCTG AATATAACAA CCTTTAAAAA AGCAAAATAA
 961 TAAGAAGGAA AAATTCCAGG AGGGAAAATG AATTGTCTTC ACTCTTCATT CTTTGAAGGA
1021 TTTACTGCAA GAAGTACATG AAGAGCAGCT GGTCAACCTG CTCACTGTTC TATCTCCAAA
1081 TGAGACACAT TAAAGGGTAG CCTACAAATG TTTTCAGGCT TCTTTCAAAG TGTAAGCACT
1141 TCTGAGCTGCTTTAGCATTGA AGTGTCGAAA GCAACTCACA CGGGAAGATC ATTTCTTATT
1201 TGTGCTCTGT GACTGCCAAG GTGTGGCCTG CACTGGGTTG TCCAGGGAGA CATGCATCTA
1261 GTGCTGTTTC TCCCACATAT TCACATACGT GTCTGTGTGT ATATATATTT TTTCAATTTA
1321 AAGGTTAGTA TGGAATCAGC TGCTACAAGA ATGCAAAAAA TCTTCCAAAG ACAAGAAAAG
1381 AGGAAAAAAA GCCGTTTTCA TGAGCTGAGT GATGTAGCGT AACAAACAAA ATCATGGAGC
1441 TGAGGAGGTG CCTTGTAAAC ATGAAGGGGC AGATAAAGGA AGGAGATACT CATGTTGATA
1501 AAGAGAGCCC TGGTCCTAGA CATAGTTCAG CCACAAAGTA GTTGTCCCTT TGTGGACAAG
1561 TTTCCCAAAT TCCCTGGACC TCTGCTTCCC CATCTGTTAA ATGAGAGAAT AGAGTATGGT
1621 TGATTCCCAG CATTCAGTGG TCCTGTCAAG CAACCTAACA GGCTAGTTCT AATTCCCTAT
1681 TGGGTAGATG AGGGGATGAC AAAGAACAGT TTTTAAGCTA TATAGGAAAC ATTGTTATTG
1741 GTGTTGCCCT ATCGTGATTT CAGTTGAATT CATGTGAAAA TAATAGCCAT CCTTGGCCTG
1801 GCGCGGTGGC TCACACCTGT AATCCCAGCA CTTTTGGAGG CCAAGGTGGG TGGATCACCT
1861 GAGGTCAGGA GTTCAAGACC AGCCTGGCCA ACATGATGAA ACCCCGTCTC TACTAAAAAT
1921 ACAAAAAATT AGCCGGGCAT GATGGCAGGT GCCTGTAATC CCAGCTACTT GGGAGGCTGA
1981 AGCGGAAGAA TCGCTTGAAC CCAGAGGTGG AGGTTGCAGT GAGCCGAGAT CGTGCCATTG
2041 CACTGTAACC TGGGTGACTG AGCAAAACTC TGTCTCAAAA TAATAATAAC AATATAATAA
2101 TAATAATAGC CATCCTTTAT TGTACCCTTA CTGGGTTAAT CGTATTATAC CACATTACCT
2161 CATTTTAATT TTTACTGACC TGCACTTTAT ACAAAGCAAC AAGCCTCCAG GACATTAAAA
2221 TTCATGCAAA GTTATGCTCA TGTTATATTA TTTTCTTACT TAAAGAAGGA TTTATTAGTG
```

```
2281 GCTGGGCATG GTGGCGTGCA CCTGTAATCC CAGGTACTCA GGAGGCTGAG ACGGGAGAAT

2341 TGCTTGACCC CAGGCGGAGG AGGTTACAGT GAGTCGAGAT CGTACCTGAG CGACAGAGCG

2401 AGACTCCGTC TCAAAAAAAA AAAAAAGGAG GGTTTATTAA TGAGAAGTTT GGTCGAC
```

In some embodiments, the truncated FXN 3' UTR has the sequence of SEQ ID NO: 3.

```
Exemplary truncated FXN 3' UTR
                                                  (SEQ ID NO: 3)
AAGAAGGAAAAATTCCAGGAGGGAAAATGAATTGTCTTCACTCTTCATTC

TTTGAAGGATTTACTGCAAGAAGTACATGAAGAGCAGCTGGTCAACCTGC

TCACTGTTCTATCTCCAAATGAGACACATTAAAGGGTAGCCTACAAATGT

TTTCAGGCTTCTTTCAAAGTGTAAGCACTTCTGAGCTCTTTAGCATTGAA

GTGTCGAAAGCAACTCACACGGGAAGATCATTTCTTATTTGTGCTCTGTG

ACTGCCAAGGTGTGGCCTGCACTGGGTTGTCCAGGGAGACATGCATCTAG

TGCTGTTTCTCCCACATATTCACATACGTGTCTGTGTGTATATATATTTT

TTCAATTTAAAGGTTAGTATGGAATCAGCTGCTACAAGAATGCAAAAAAT

CTTCCAAAGACAAGAAAAGAGGAAAAAAAGCCGTTTTCATGAGCTGAGTG

ATGTAGCGTAACAAACAAAATCATGGAGCTGAGGAGGTGCCTTGTAAACA

TGAAGGGGCAGATAAAGGAAGGAGATACTCATGTTGATAAAGAGAGCCCT

GGTCCTAGACATAGTTCAGCCACAAAGTAGTTGTCCCTTTGTGGACAAGT

TTCCCAAATTCCCTGGACCTCTGCTTCCCCATCTGTTAAATGAGAGAATA

GAGTATGGTTGATTCCCAGCATTCAGTGGTCCTGTCAAGCAACCTAACAG

GCTAGTTCTAATTCCCTATTGGGTAGATGAGGGGATGACAAAGAACAGTT

TTTAAGCTATATAGGAAACATTGTTATTGGTGTTGCCCTATCGTGATTTC

AGTTGAATTCATGTGAAAATAATAGCCATCCTTGGCCTGGCGCGGTGGCT

CACACCTGTAATCCCAGCACTTTTGGAGGCCAAGGTGGGTGGATCACCTG

AGGTCAGGAGTTCAAGACCAGCCTGGCCAACATGATGAAACCCCGTCTCT

ACTAAAAATACAAAAAATTAGCCGGGCATGATGGCAGGTGCCTGTAATCC

CAGCTACTTGGGAGGCTGAAGCGGAAGAATCGCTTGAACCCAGAGGTGGA

GGTTGCAGTGAGCCGAGATCGTGCCATTGCACTGTAACCTGGGTGACTGA

GCAAAACTCTGTCTCAAAATAATAATAACAATATAATAATAATAATAGCC

ATCCTTTATTGTACCCTTACTGGGTTAATCGTATTATACCACATTACCTC

ATTTTAATTTTTACTGACCTGCACTTTATACAAAGCAACAAGCCTCCAGG

ACATTAAAATTCATGCAAAGTTATGCTCATGTTATATTATTTTCTTACTT

AAAGAAGGATTTATTAGTGGCTGGGCATGGTGGCGTGCACCTGTAATCCC

AGGTACTCAGGAGGCTGAGACGGGAGAATTGCTTGACCCCAGGCGGAGGA

GGTTACAGTGAGTCGAGATCGTACCTGAGCGACAGAGCGAGACTCCGTCT

CAAAAAAAAAAAAAGGAGGGTTTATTAATGAGAAGTTTG
```

In some embodiments, the expression construct further contains a nucleic acid segment that encode a polyadenylation signal. In some embodiments, the nucleic acid segment is positioned 3' to the FXN 3' UTR in the expression construct.

In some embodiments, the expression construct comprises the sequence of SEQ ID NO: 4 (or a portion thereof comprising a gene of interest under the control of a promoter of interest, optionally flanked by ITR sequences).

```
Exemplary expression construct
                                                  (SEQ ID NO: 4)
GATCTTACCCCCTGCCCCCCACAGCTCCTCTCCTGTGCCTTGTTTCCCAG

CCATGCGTTCTCCTCTATAAATACCCGCTCTGGTATTTGGGGTTGGCAGC

TGTTGCTGCCAGGGAGATGGTTGGGTTGACATGCGGCTCCTGACAAAACA

CAAACCCCTGGTGTGTGTGGGCGTGGGTGGTGTGAGTAGGGGGATGAATC

AGGGAGGGGGCGGGGGACCCAGGGGGCAGGAGCCACACAAAGTCTGTGCG

GGGGTGGGAGCGCACATAGCAATTGGAAACTGAAAGCTTATCAGACCCTT

TCTGGAAATCAGCCCACTGTTTATAAACTTGAGGCCCCACCCTCGAGATA

ACCAGGGCTGAAAGAGGCCCGCCTGGGGGCTGGAGACATGCTTGCTGCCT

GCCCTGGCGAAGGATTGGCAGGCTTGCCCGTCACAGGACCCCCGCTGGCT

GACTCAGGGGCGCAGGCCTCTTGCGGGGGAGCTGGCCTCCCCGCCCCCAC

GGCCACGGGCCGCCCTTTCCTGGCAGGACAGCGGGATCTTGCAGCTGTCA

GGGGAGGGGAGGCGGGGGCTGATGTCAGGAGGGATACAAATAGTGCCGAC

GGCTGGGGCCCTGTCTCCCCTCGCCGCATCCACTCTCCGGCCGGCCGCC

TGTCCGCCGCCTCCTCCGTGCGCCCGCCAGCCTCGCCCGCGCCGTCACCG

TGAGGCACTGGGCAGGTAAGTATCAAAGTATCAAGGTTACAAGACAGGTT

TAAGGAGACCAATAGAAACTGGGCTTGTCGAGACAGAGAAGACTCTTGCG

TTTCTGATAGGCACCTATTGGTCTTACTGACATCCACTTTGCCTTTCTCT

CCACAGGCTAGCCTCGAGAATTCACGCGTGGTACCTCTAGAGTCGACCGA

TATCACTAGTGCCACCATGTGGACACTGGGGAGAAGGGCCGTGGCTGGAC

TGCTGGCTTCTCCATCTCCAGCCCAGGCCCAGACCCTGACCAGAGTGCCT

AGACCTGCCGAACTGGCCCCTCTGTGTGGCAGAAGAGGCCTGAGAACCGA

CATCGACGCCACCTGTACCCCCAGAAGGGCCAGCAGCAATACGCGGGCC

TGAATCAGATCTGGAACGTGAAGAAACAGAGCGTGTACCTGATGAACCTG

AGAAAGAGCGGCACCCTGGGCCACCCTGGAAGCCTGGATGAGACAACCTA

CGAGCGGCTGGCCGAGGAAACCCTGGATTCCCTGGCCGAGTTCTTCGAGG

ACCTGGCCGACAAGCCCTACACCTTCGAGGATTACGACGTGTCCTTCGGC

AGCGGCGTGCTGACAGTGAAGCTGGGCGGAGATCTGGGCACCTACGTGAT

CAACAAGCAGACCCCCAACAAACAGATCTGGCTGAGCAGCCCCAGCAGCG

GCCCCAAGAGATACGATTGGACCGGCAAGAACTGGGTGTTCAGCCACGAC

GGCGTGTCCCTGCATGAGCTGCTGGCTGCCGAGCTGACCAAGGCCCTGAA

AACAAAGCTGGACCTGAGCTGGCTGGCCTACAGCGGCAAAGATGCCATCG

ATATCCCCAGCCCCGTTTTAAGGACATTAAAAGCTATCAGGCCAAGACCC
```

CAGCTTCATTATGCAGCTGAGGTCTGTTTTTTGTTGTTGTTGTTTAT

TTTTTTTATTCCTGCTTTTGAGGACAGTTGGGCTATGTGTCACAGCTCTG

TAGAAAGAATGTGTTGCCTCCTACCTTGCCCCCAAGTTCTGATTTTTAAT

TTCTATGGAAGATTTTTTGGATTGTCGGATTTCCTCCCTCACATGATACC

CCTTATCTTTTATAATGTCTTATGCCTATACCTGAATATAACAACCTTTA

AAAAAGCAAAATAATAAGAAGGAAAAATTCCAGGAGGGAAAATGAATTGT

CTTCACTCTTCATTCTTTGAAGGATTTACTGCAAGAAGTACATGAAGAGC

AGCTGGTCAACCTGCTCACTGTTCTATCTCCAAATGAGACACATTAAAGG

GTAGCCTACAAATGTTTTCAGGCTTCTTTCAAAGTGTAAGCACTTCTGAG

CTCTTTAGCATTGAAGTGTCGAAAGCAACTCACACGGGAAGATCATTTCT

TATTTGTGGTCTGTGACTGCCAAGGTGTGGCCTGCACTGGGTTGTCCAGG

GAGACATGCATCTAGTGCTGTTTCTCCCACATATTCACATACGTGTCTGT

GTGTATATATATTTTTTCAATTTAAAGGTTAGTATGGAATCAGCTGCTAC

AAGAATGCAAAAAATCTTCCAAAGACAAGAAAAGAGGAAAAAAAGCCGTT

TTCATGAGCTGAGTGATGTAGCGTAACAAACAAAATCATGGAGCTGAGGA

GGTGCCTTGTAAACATGAAGGGGCAGATAAAGGAAGGAGATACTCATGTT

GATAAAGAGAGCCCTGGTCCTAGACATAGTTCAGCCACAAAGTAGTTGTC

CCTTTGTGGACAAGTTTCCCAAATTCCCTGGACCTCTGCTTCCCCATCTG

TTAAATGAGAGAATAGAGTATGGTTGATTCCCAGCATTCAGTGGTCCTGT

CAAGCAACCTAACAGGCTAGTTCTAATTCCCTATTGGGTAGATGAGGGGA

TGACAAAGAACAGTTTTTAAGCTATATAGGAAACATTGTTATTGGTGTTG

CCCTATCGTGATTTCAGTTGAATTCATGTGAAAATAATAGCCATCCTTGG

CCTGGCGCGGTGGCTCACACCTGTAATCCCAGCACTTTTGGAGGCCAAGG

TGGGTGGATCACCTGAGGTCAGGAGTTCAAGACCAGCCTGGCCAACATGA

TGAAACCCCGTCTCTACTAAAAATACAAAAAATTAGCCGGGCATGATGGC

AGGTGCCTGTAATCCCAGCTACTTGGGAGGCTGAAGCGGAAGAATCGCTT

GAACCCAGAGGTGGAGGTTGCAGTGAGCCGAGATCGTGCCATTGCACTGT

AACCTGGGTGACTGAGCAAAACTCTGTCTCAAAATAATAATAACAATATA

ATAATAATAATAGCCATCCTTTATTGTACCCTTACTGGGTTAATCGTATT

ATACCACATTACCTCATTTTAATTTTTACTGACCTGCACTTTATACAAAG

CAACAAGCCTCCAGGACATTAAAATTCATGCAAAGTTATGCTCATGTTAT

ATTATTTTCTTACTTAAAGAAGGATTTATTAGTGGCTGGGCATGGTGGCG

TGCACCTGTAATCCCAGGTACTACGGAGGCTGAGACGGGAGAATTGCTTG

ACCCCAGGCGGAGGAGGTTACAGTGAGTCGAGATCGTACCTGAGCGACAG

AGCGAGACTCCGTCTCAAAAAAAAAAAAAAGGAGGGTTTATTAATGAGAA

GTTTGGTCGACTAGAGCGGCCGCTTCGAGCAGACATGATAAGATACATTG

ATGAGTTTGGACAAACCACAACTAGAATGCAGTGAAAAAAATGCTTTATT

ATTCATTTTATGTTTCAGGTTCAGGGGGAGATGTGGGAGGTTTTTTAAAG

CAAGTAAAACCTCTACAAATGTGGTA

In some embodiments, the nucleic acid is a plasmid. In some embodiments, the nucleic acid comprises or consists of the sequence of SEQ ID NO 5.

Exemplary plasmid sequence
(SEQ ID NO: 5)
CTGCAGGGGGGGGGGGGGGGGTTGGCCACTCCCTCTCTGCGCGCTCGCTCGCTCACTGAGGCCGGGCGACCAA

AGGTCGCCCGACGCCCGGGCTTTGCCCGGGCGGCCTCAGTGAGCGAGCGAGCGCGCAGAGAGGGAGTGGCCAACT

CCATCACTAGGGGTTCCTCAGATCTTACCCCCTGCCCCCCACAGCTCCTCTCCTGTGCCTTGTTTCCCAGCCATG

CGTTCTCCTCTATAAATACCCGCTCTGGTATTTGGGGTTGGCAGCTGTTGCTGCCAGGGAGATGGTTGGGTTGAC

ATGCGGCTCCTGACAAAACACAAACCCCTGGTGTGTGTGGGCGTGGGTGGTGTGAGTAGGGGGATGAATCAGGGA

GGGGGCGGGGACCCAGGGGGCAGGAGCCACACAAAGTCTGTGCGGGGGTGGGAGCGCACATAGCAATTGGAAAC

TGAAAGCTTATCAGACCCTTTCTGGAAATCAGCCCACTGTTTATAAACTTGAGGCCCCACCCTCGAGATAACCAG

GGCTGAAAGAGGCCCGCCTGGGGGCTGGAGACATGCTTGCTGCCTGCCCTGGCGAAGGATTGGCAGGCTTGCCCG

TCACAGGACCCCGCTGGCTGACTCAGGGGCGCAGGCCTCTTGCGGGGGAGCTGGCCTCCCCGCCCCCACGGCCA

CGGGCCGCCCTTTCCTGGCAGGACAGCGGGATCTTGCAGCTGTCAGGGGAGGGGAGGCGGGGCTGATGTCAGGA

GGGATACAAATAGTGCCGACGGCTGGGGGCCCTGTCTCCCCTCGCCGCATCCACTCTCCGGCCGGCCGCCTGTCC

GCCGCCTCCTCCGTGCGCCCGCCAGCCTCGCCCGCGCCGTCACCGTGAGGCACTGGGCAGGTAAGTATCAAAGTA

TCAAGGTTACAAGACAGGTTTAAGGAGACCAATAGAAACTGGGCTTGTCGAGACAGAGAAGACTCTTGCGTTTCT

GATAGGCACCTATTGGTCTTACTGACATCCACTTTGCCTTTCTCTCCACAGGCTAGCCTCGAGAATTCACGCGTG

GTACCTCTAGAGTCGACCGATATCACTAGTGCCACCATGTGGACACTGGGGAGAAGGGCCGTGGCTGGACTGCTG

GCTTCTCCATCTCCAGCCCAGGCCCAGACCCTGACCAGAGTGCCTAGACCTGCCGAACTGGCCCCTCTGTGTGGC

AGAAGAGGCCTGAGAACCGACATCGACGCCACCTGTACCCCCAGAAGGGCCAGCAGCAATCAGCGGGGCCTGAAT

-continued

```
CAGATCTGGAACGTGAAGAAACAGAGCGTGTACCTGATGAACCTGAGAAAGAGCGGCACCCTGGGCCACCCTGGA

AGCCTGGATGAGACAACCTACGAGCGGCTGGCCGAGGAAACCCTGGATTCCCTGGCCGAGTTCTTCGAGGACCTG

GCCGACAAGCCCTACACCTTCGAGGATTACGACGTGTCCTTCGGCAGCGGCGTGCTGACAGTGAAGCTGGGCGGA

GATCTGGGCACCTACGTGATCAACAAGCAGACCCCCAACAAACAGATCTGGCTGAGCAGCCCCAGCAGCGGCCCC

AAGAGATACGATTGGACCGGCAAGAACTGGGTGTTCAGCCACGACGGCGTGTCCCTGCATGAGCTGCTGGCTGCC

GAGCTGACCAAGGCCCTGAAAACAAAGCTGGACCTGAGCTGGCTGGCCTACAGCGGCAAAGATGCCATCGATATC

CCCAGCCCCGTTTTAAGGACATTAAAAGCTATCAGGCCAAGACCCCAGCTTCATTATGCAGCTGAGGTCTGTTTT

TTGTTGTTGTTGTTGTTTATTTTTTTATTCCTGCTTTTGAGGACAGTTGGGCTATGTGTCACAGCTCTGTAGAA

AGAATGTGTTGCCTCCTACCTTGCCCCCAAGTTCTGATTTTTAATTTCTATGGAAGATTTTTTGGATTGTCGGAT

TTCCTCCCTCACATGATACCCCTTATCTTTTATAATGTCTTATGCCTATACCTGAATATAACAACCTTTAAAAAA

GCAAGAAGTACATGAAGAGCAGCTGGTCAACCTGCTCACTGTTCTATCTCCAAATGAGACACATTAAAGGGTAGC

GCAAGAAGTACATGAAGAGCAGCTGGTCAACCTGCTCACTGTTCTATCTCCAAATGAGACACATTAAAGGGTAGC

CTACAAATGTTTTCAGGCTTCTTTCAAAGTGTAAGCACTTCTGAGCTCTTTAGCATTGAAGTGTCGAAAGCAACT

CACACGGGAAGATCATTTCTTATTTGTGCTCTGTGACTGCCAAGGTGTGGCCTGCACTGGGTTGTCCAGGGAGAC

ATGCATCTAGTGCTGTTTCTCCCACATATTCACATACGTGTCTGTGTGTATATATATTTTTTCAATTTAAAGGTT

AGTATGGAATCAGCTGCTACAAGAATGCAAAAAATCTTCCAAAGACAAGAAAAGAGGAAAAAAAGCCGTTTTCAT

GAGCTGAGTGATGTAGCGTAACAAACAAAATCATGGAGCTGAGGAGGTGCCTTGTAAACATGAAGGGGCAGATAA

AGGAAGGAGATACTCATGTTGATAAAGAGAGCCCTGGTCCTAGACATAGTTCAGCCACAAAGTAGTTGTCCCTTT

GTGGACAAGTTTCCCAAATTCCCTGGACCTCTGCTTCCCCATCTGTTAAATGAGAGAATAGAGTATGGTTGATTC

CCAGCATTCAGTGGTCCTGTCAAGCAACCTAACAGGCTAGTTCTAATTCCCTATTGGGTAGATGAGGGGATGACA

AAGAACAGTTTTTAAGCTATATAGGAAACATTGTTATTGGTGTTGCCCTATCGTGATTTCAGTTGAATTCATGTG

AAAATAATAGCCATCCTTGGCCTGGCGCGGTGGCTCACACCTGTAATCCCAGCACTTTTGGAGGCCAAGGTGGGT

GGATCACCTGAGGTCAGGAGTTCAAGACCAGCCTGGCCAACATGATGAAACCCCGTCTCTACTAAAAATACAAAA

AATTAGCCGGGCATGATGGCAGGTGCCTGTAATCCCAGCTACTTGGGAGGCTGAAGCGGAAGAATCGCTTGAACC

CAGAGGTGGAGGTTGCAGTGAGCCGAGATCGTGCCATTGCACTGTAACCTGGGTGACTGAGCAAAACTCTGTCTC

AAAATAATAATAACAATATAATAATAATAATAGCCATCCTTTATTGTACCCTTACTGGGTTAATCGTATTATACC

ACATTACCTCATTTTAATTTTTACTGACCTGCACTTTATACAAAGCAACAAGCCTCCAGGACATTAAAATTCATG

CAAAGTTATGCTCATGTTATATTATTTTCTTACTTAAAGAAGGATTTATTAGTGGCTGGGCATGGTGGCGTGCAC

CTGTAATCCCAGGTACTCAGGAGGCTGAGACGGGAGAATTGCTTGACCCCAGGCGGAGGAGGTTACAGTGAGTCG

AGATCGTACCTGAGCGACAGAGCGAGACTCCGTCTCAAAAAAAAAAAAAAGGAGGGTTTATTAATGAGAAGTTTG

GTCGACTAGAGCGGCCGCTTCGAGCAGACATGATAAGATACATTGATGAGTTTGGACAAACCACAACTAGAATGC

AGTGAAAAAAATGCTTTATTTGTGAAATTTGTGATGCTATTGCTTTATTTGTAACCATTATAAGCTGCAATAAAC

AAGTTAACAACAACAATTGCATTCATTTTATGTTTCAGGTTCAGGGGGAGATGTGGGAGGTTTTTTAAAGCAAGT

AAAACCTCTACAAATGTGGTAAAATCGATAAGGATCTAGGAACCCCTAGTGATGGAGTTGGCCACTCCCTCTCTG

CGCGCTCGCTCGCTCACTGAGGCCGCCCGGGCAAAGCCCGGGCGTCGGGCGACCTTTGGTCGCCCGGCCTCAGTG

AGCGAGCGAGCGCGCAGAGAGGGAGTGGCCAACCCCCCCCCCCCCCCCCCTGCAGCCTGGCGTAATAGCGAAGAG

GCCCGCACCGATCGCCCTTCCCAACAGTTGCGTAGCCTGAATGGCGAATGGCGCGACGCGCCCTGTAGCGGCGCA

TTAAGCGCGGCGGGTGTGGTGGTTACGCGCAGCGTGACCGCTACACTTGCCAGCGCCCTAGCGCCCGCTCCTTTC

GCTTTCTTCCCTTCCTTTCTCGCCACGTTCGCCGGCTTTCCCCGTCAAGCTCTAAATCGGGGGCTCCCTTTAGGG

TTCCGATTTAGTGCTTTACGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGACTCTTGTTCCAAACTGGA
```

-continued

```
ACAACACTCAACCCTATCTCGGTCTATTCTTTTGATTTATAAGGGATTTTGCCGATTTCGGCCTATTGGTTAAAA

AATGAGCTGATTTAACAAAAATTTAACGCGAATTTTAACAAAATATTAACGTTTACAATTTCCTGATGCGGTATT

TTCTCCTTACGCATCTGTGCGGTATTTCACACCGCATATGGTGCACTCTCAGTACAATCTGCTCTGATGCCGCAT

AGTTAAGCCAGCCCCGACACCCGCCAACACCCGCTGACGCGCCCTGACGGGCTTGTCTGCTCCCGGCATCCGCTT

ACAGACAAGCTGTGACCGTCTCCGGGAGCTGCATGTGTCAGAGGTTTTCACCGTCATCACCGAAACGCGCGAGAC

GAAAGGGCCTCGTGATACGCCTATTTTTATAGGTTAATGTCATGATAATAATGGTTTCTTAGACGTCAGGTGGCA

CTTTTCGGGGAAATGTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTATGAGTATTCAACATTTCCGTGTCGCCC

TTATTCCCTTTTTTGCGGCATTTTGCCTTCCTGTTTTTGCTCACCCAGAAACGCTGGTGAAAGTAAAAGATGCTG

AAGATCAGTTGGGTGCACGAGTGGGTTACATCGAACTGGATCTCAACAGCGGTAAGATCCTTGAGAGTTTTCGCC

CCGAAGAACGTTTTCCAATGATGAGCACTTTTAAAGTTCTGCTATGTGGCGCGGTATTATCCCGTATTGACGCCG

GGCAAGAGCAACTCGGTCGCCGCATACACTATTCTCAGAATGACTTGGTTGAGTACTCACCAGTCACAGAAAAGC

ATCTTACGGATGGCATGACAGTAAGAGAATTATGCAGTGCTGCCATAACCATGAGTGATAACACTGCGGCCAACT

TACTTCTGACAACGATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATGCCTGTAGCAATGG

CAACAACGTTGCGCAAACTATTAACTGGCGAACTACTTACTCTAGCTTCCCGGCAACAATTAATAGACTGGATGG

AGGCGGATAAAGTTGCAGGACCACTTCTGCGCTCGGCCCTTCCGGCTGGCTGGTTTATTGCTGATAAATCTGGAG

CCGGTGAGCGTGGGTCTCGCGGTATCATTGCAGCACTGGGGCCAGATGGTAAGCCCTCCCGTATCGTAGTTATCT

ACACGACGGGGAGTCAGGCAACTATGGATGAACGAAATAGACAGATCGCTGAGATAGGTGCCTCACTGATTAAGC

ATTGGTAACTGTCAGACCAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATCTGCTGCTTGCAAACAAAAA

AACCACCGCTACCAGCGGTGGTTTGTTTGCCGGATCAAGAGCTACCAACTCTTTTTCCGAAGGTAACTGGCTTCA

GCAGAGCGCAGATACCAAATACTGTCCTTCTAGTGTAGCCGTAGTTAGGCCACCACTTCAAGAACTCTGTAGCAC

CGCCTACATACCTCGCTCTGCTAATCCTGTTACCAGTGGCTGCTGCCAGTGGCGATAAGTCGTGTCTTACCGGGT

TGGACTCAAGACGATAGTTACCGGATAAGGCGCAGCGGTCGGGCTGAACGGGGGGTTCGTGCACACAGCCCAGCT

TGGAGCGAACGACCTACACCGAACTGAGATACCTACAGCGTGAGCATTGAGAAAGCGCCACGCTTCCCGAAGGGA

GAAAGGCGGACAGGTATCCGGTAAGCGGCAGGGTCGGAACAGGAGAGCGCACGAGGGAGCTTCCAGGGGGAAACG

CCTGGTATCTTTATAGTCCTGTCGGGTTTCGCCACCTCTGACTTGAGCGTCGATTTTTGTGATGCTCGTCAGGGG

GGCGGAGCCTATGGAAAAACGCCAGCAACGCGGCCTTTTTACGGTTCCTGGCCTTTTGCTGGCCTTTTGCTCACA

TGTTCTTTCCTGCGTTATCCCCTGATTCTGTGGATAACCGTATTACCGCCTTTGAGTGAGCTGATACCGCTCGCC

GCAGCCGAACGACCGAGCGCAGCGAGTCAGTGAGCGAGGAAGCGGAAGAGCGCCCAATACGCAAACCGCCTCTCC

CCGCGCGTTGGCCGATTCATTAATGCAGGG
```

In some embodiments, the nucleic acid is a recombinant adeno-associated virus (rAAV) vector. Exemplary rAAV nucleic acid vectors useful according to the disclosure include single-stranded (ss) or self-complementary (sc) AAV nucleic acid vectors.

In some embodiments, a recombinant rAAV particle comprises (or packages) a nucleic acid vector that comprises an expression construct, such as a single-stranded (ss) or self-complementary (sc) AAV nucleic acid vector. In some embodiments, the nucleic acid vector comprises an expression construct comprising FXN coding sequence (e.g., a human FXN coding sequence) and a truncated FXN 3' UTR (e.g., a truncated human FXN 3' UTR) operably linked to a promoter (e.g., a Desmin promoter, a CBA promoter, a hFXNPro, or other promoter) and is flanked by regions comprising inverted terminal repeat (ITR) sequences (e.g., wild-type ITR sequences or engineered ITR sequences). In some embodiments, the nucleic acid is encapsidated by a viral capsid.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

The ITR sequences of a nucleic acid or nucleic acid vector described herein can be derived from any AAV serotype (e.g., 1, 2, 3, 4, 5, 6, 7, 8, 9, 10, 11, 12, or 13) or can be derived from more than one serotype. In some embodiments of the nucleic acid or nucleic acid vector provided herein, the ITR sequences are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, the nucleic acid or nucleic acid vector comprises a pTR-UF-11 plasmid backbone, which is a plasmid that contains AAV2 ITRs, or a nucleic acid region of the pTR-UF-11 plasmid that comprises the ITRs. This plasmid is commercially available from the American Type Culture Collection (ATCC MBA-331). One or more genes of interest (for example encoding a therapeutic protein) under the control of a promoter of interest (for example a Desmin promoter or derivative thereof described in this application) can be inserted in between the ITRs in one these or other plasmids containing AAV ITRs. These can be used as described in this application to produce a rAAV particle encapsidating a rAAV nucleic acid comprising ITRs flanking a gene of interest under the control of a promoter of interest.

Genebank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

In some embodiments, the expression construct is no more than 7 kilobases, no more than 6 kilobases, no more than 5 kilobases, no more than 4 kilobases, or no more than 3 kilobases in size. In some embodiments, the expression construct is between 4 and 7 kilobases in size.

In some embodiments, the expression construct comprises one or more regions comprising a sequence that facilitates expression of the FXN coding sequence, e.g., expression control sequences operably linked to the FXN coding sequence. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer). In some embodiments, the promoter is a Desmin promoter as described herein. In some embodiments, the expression construct contains a splice donor/acceptor site, such as between the promoter and the FXN coding sequence.

To achieve appropriate expression levels of FXN, any of a number of promoters suitable for use in the selected host cell may be employed. The promoter may be, for example, a constitutive promoter, tissue-specific promoter, inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter.

Inducible promoters and/or regulatory elements may also be contemplated for achieving appropriate expression levels of FXN. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include hematopoietic stem cell-specific promoters.

Synthetic promoters are also contemplated herein. A synthetic promoter may comprise, for example, regions of known promoters, regulatory elements, transcription factor binding sites, enhancer elements, repressor elements, and the like.

Although the use of AAV has advanced in recent years, gene transfer still faces some obstacles. For example, tissue specific targeting to deliver the gene to affected organs or to avoid toxicity remains a challenge. High levels of overexpression driven by a strong promoter can lead to toxicity in vitro. In this context, organ specificity of different promoters can be taken advantage of to achieve sufficient gene delivery to target organs while avoiding complications related to administration of high doses. In some embodiments, identification of the most efficient and safe promoter element for the transcriptional control of the FXN transgene can be used to correct FXN deficiency in the heart, CNS and in the pancreatic islet cells. Thus, in some embodiments, the promoter in the disclosed nucleic acid is a human Desmin promoter or a derivative thereof. The Desmin promoter is a tissue-restricted promoter for cardiac muscle and neurons. The Desmin promoter element is a derivative of the Desmin gene control element, which contains additional transcriptional control elements to augment expression. In some embodiments, the promoter in the disclosed nucleic acid is the chicken β-actin (CBA) promoter. In some embodiments, the CBA promoter is a constitutive element made up of the cytomegalovirus (CMV) immediate early enhancer element, the beta-actin promoter and globin intron. In some embodiments, the CBA promoter allows targeting of muscle, neurons and the pancreas for FXN transgene delivery. In some embodiments, the promoter in the disclosed nucleic acid is the endogenous frataxin promoter (FxP), hFXNPro, which has been mapped to encompass a 1 kb region 5' to the frataxin transcriptional start site. In some embodiments, the promoter in the disclosed nucleic acid is the endogenous frataxin promoter (FxP), hFXNPro, which has been mapped to encompass a 1.220 kb region 5' to the frataxin transcriptional start site. In some embodiments, no remote enhancer elements are required, and all the necessary transcriptional control and tissue restricted activity are conferred by the frataxin promoter. However, additional regulatory sequences can be used in some embodiments. In some embodiments, the CBA promoter and the hFXNPro allow targeting of the pancreatic islet cells for FXN gene delivery. In some embodiments, the nucleic acid is a plasmid (e.g., a circular nucleic acid comprising one or more of an origin of replication, a selectable marker, and a reporter gene). In some embodiments, a nucleic acid described herein, such as a plasmid, may also contain marker or reporter genes, e.g., LacZ or a fluorescent protein, and an origin of replication. In some embodiments, the plasmid is transfected into a producer cell that produces AAV particles containing the expression construct (e.g., the expression construct that was included in the plasmid that was used to produce the nucleic acid that was encapsidated by the rAAV particles).

The rAAV particle may be of any AAV serotype (e.g., 1, 2, 3, 4, 5, 6, 7, 8, 9, 10, 11, 12, or 13), including any derivative (including non-naturally occurring variants of a serotype) or pseudotype. In some embodiments, the rAAV particle is an AAV9 particle, which may be pseudotyped with AAV2 ITRs. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A 1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al., Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector (e.g., as a plasmid) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the packaging is performed in a helper cell or producer cell, such as a mammalian cell or an insect cell. Exemplary mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC© CRL-1711™). The helper cell may comprises rep and/or cap genes that encode the Rep protein and/or Cap proteins for use in a method described herein. In some embodiments, the packaging is performed in vitro.

In some embodiments, the one or more helper plasmids includes a first helper plasmid comprising a rep gene and a cap gene and a second helper plasmid comprising other genes that assist in AAV production, such as a E1a gene, a E1b gene, a E4 gene, a E2a gene, and a VA gene. In some embodiments, the rep gene is a rep gene derived from AAV2 and the cap gene is derived from AAV5. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adenoassociated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector described herein. Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise at least one of the disclosed rAAV particles, expression constructs, or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Compositions

Aspects of the disclosure relate to compositions comprising rAAV particles or nucleic acids described herein. In some embodiments, rAAV particles described herein are added to a composition, e.g., a pharmaceutical composition.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, $22^{nd}$ edition, Pharmaceutical Press, 2012.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, a composition described herein may be administered to a subject in need thereof, such as a subject having Friedreich's ataxia. In some embodiments, a method described herein may comprise administering a composition comprising rAAV particles as described herein to a subject in need thereof. In some embodiments, the subject is a human subject. In some embodiments, the subject has or is suspected of having a disease that may be treated with gene therapy, such as Friedreich's ataxia.

Methods

Aspects of the disclosure relate to treatment of Friedreich's ataxia. In some embodiments, the method comprises administering a therapeutically effective amount of an rAAV particle or a composition as described herein to a subject having Friedreich's ataxia.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., Friedreich's ataxia. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The rAAV particle or nucleic acid vector may be delivered in the form of a composition, such as a composition comprising the active ingredient, such as a rAAV particle described herein, and a pharmaceutically acceptable carrier as described herein. The rAAV particles or nucleic acid vectors may be prepared in a variety of compositions, and may also be formulated in appropriate pharmaceutical vehicles for administration to human or animal subjects.

In some embodiments, the number of rAAV particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, rAAV particles of higher than $10^{13}$ particles/ml are be administered. In some embodiments, the number of rAAV particles administered to a subject may be on the order ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, rAAV particles of higher than $10^{13}$ vgs/ml are be administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/mg. In some embodiments, the number of rAAV particles administered to a subject may be on the order ranging from $10^{12}$-$10^{14}$ vgs/kg.

If desired, rAAV particles may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized.

In certain circumstances it will be desirable to deliver the rAAV particles in suitably formulated pharmaceutical compositions disclosed herein either subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection. In some embodiments, the administration is a route suitable for systemic delivery, such as by intravenous injection. In some embodiments, "administering" or "administration" means providing a material to a subject in a manner that is pharmacologically useful.

To address the systemic manifestations of FRDA, approaches to transfer AAV vectors globally that target both the neurological and cardiac impairment may be needed. Although IV dosing is an advantageous route to transduce the heart, it does not have high translational feasibility for CNS disorders because of the high dose requirement, high distribution to peripheral tissues and reduced efficiency for CNS transduction (Schuster, D. et al., Front Neuronat., 8:42, 2014). However, intrathecal (IT) dosing of AAV9 (e.g., via lumbar cistern or cisterna magna) is a viable, clinically relevant option for global CNS gene delivery (Gray, S. et al., Gene Ther, 20(4):450-9, 2013; Federici, T. et al., Gene Ther, 19(8):852, 2012; Snyder, B. et al., Hum Gene Ther, 22(9): 1129, 2011). A method of treating subjects with FRDA using a combination of different routes of administration (e.g., IV and IT), by transduction of cardiac muscle, pancreas (e.g., pancreatic islet cells), and CNS (e.g., dorsal root ganglia, and the cerebellum) is contemplated herein. Thus, in some embodiments, rAAV particles or compositions comprising rAAV particles that comprise (or package) FXN transgene are administered via intravenous (IV) injection. In some embodiments, rAAV particles or compositions comprising rAAV particles that comprise (or package) FXN transgene are administered via intrathecal (IT) injection. In some embodiments, rAAV particles or compositions comprising rAAV particles that comprise (or package) FXN transgene are administered via intracisternal injection, so as to deliver the rAAV particles within a cistern of the brain. In some embodiments, rAAV particles or compositions comprising rAAV particles that package FXN transgene are administered via both an intravenous injection and an intrathecal injection, or via an intravenous injection and an intracisternal injection.

In some embodiments, more than two (e.g., three, or four) of the above described routes of administration are utilized.

In some embodiments, the ratio of rAAV particles administered to the subject via intravenous injection to rAAV particles administered to the subject via intrathecal injection is in the range of 10:1 to 1:10 (e.g., 10:1, 8:1, 5:1, 4:1, 2:1, 1:1, 1:2, 1:5, 1:8, 1:10), or 50:1 to 1:50 (e.g., 50:1, 40:1, 25:1, 30:1, 10:1, 1:1, 1:10, 1:30, 1:25, 1:40, 1:50), or 100:1 to 1:100 (e.g., 100:1, 80:1, 50:1, 10:1, 1:1, 1:10, 1:50, 1:80, 1:100), or 1000:1 to 1:1000 (e.g., 1000:1, 800:1, 500:1, 100:1, 1:1, 1:100, 1:500, 1:800, 1:1000). In some embodiments, the ratio of rAAV particles administered to the subject via intravenous injection to rAAV particles admin-istered to the subject via intracisternal injection is in the range of 10:1 to 1:10 (e.g., 10:1, 8:1, 5:1, 4:1, 2:1, 1:1, 1:2, 1:5, 1:8, 1:10), or 50:1 to 1:50 (e.g., 50:1, 40:1, 25:1, 30:1, 10:1, 1:1, 1:10, 1:30, 1:25, 1:40, 1:50), or 100:1 to 1:100 (e.g., 100:1, 80:1, 50:1, 10:1, 1:1, 1:10, 1:50, 1:80, 1:100), or 1000:1 to 1:1000 (e.g., 1000:1, 800:1, 500:1, 100:1, 1:1, 1:100, 1:500, 1:800, 1:1000). In some embodiments, the ratio of rAAV particles administered to the subject via intravenous injection to rAAV particles administered to the subject via intrathecal injection is 1:10. In some embodiments, the ratio of rAAV particles administered to the subject via intravenous injection to rAAV particles administered to the subject via intracisternal injection is 1:10. In some embodiments, compositions administered via intravenous, intrathecal, and/or intracisternal injection may have the same number of particles or viral genomes per unit volume. However, in some embodiments compositions having different titers may be used for different routes of administration. Also, different compositions having different components in addition to the viral particles may be used for different routes of administration.

The amount of rAAV particle or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle compositions, either over a relatively short, or a relatively prolonged period of time, as may be determined by the medical practitioner overseeing the administration of such compositions.

In some embodiments, when more than one route of administration is utilized, the administration of rAAV comprising FXN transgene via the two or more routes is performed simultaneously, or within 10 min of each other. In some embodiments, when more than one route of administration is utilized, the administration of rAAV comprising FXN transgene via the two or more routes is staggered, so that administration via the second route is performed 10 min, 20 min, 30 min 1 h, 2h, 3h, 4h, 5h, 6h, 8h, 12h, 18h, or 24h after the administration via the first route. In some embodiments, when more than one route of administration is utilized, the administration of rAAV comprising FXN transgene via the two or more routes is altered, so that administration via the second route replaces administration via the first route on a routine basis (e.g., for once a day schedule, administration via first route on day 1, administration via second route on day 2, administration via first route on day 3, administration via second route on day 4, and so on).

In some embodiments, the number of rAAV particles administered to a subject may be on the order ranging from $10^6$ to $10^{14}$ particles/mL or $10^3$ to $10^{13}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In some embodiments, rAAV particle compositions of lower than $10^7$ particles/mL, for example lower than $10^3$ particles/mL, are administered. In some embodiments, rAAV particle compositions of higher than $10^{13}$ particles/mL, for example higher than $10^{15}$ particles/mL, are administered. In some embodiments, the number of rAAV particles administered to a subject may be on the order ranging from $10^6$ to $10^{14}$ vector genomes(vgs)/mL or $10^3$ to $10^{15}$ vgs/mL, or any values there between for either range, such as for example, about $10^6$, $10^7$, $10^8$, $10^9$, $10^{10}$, $10^{11}$, $10^{12}$, $10^{13}$, or $10^{14}$ vgs/mL. In some embodiments, rAAV particle compositions of lower than $10^7$ vgs/mL, for example lower than $10^3$ vgs/mL, are be administered. In some embodiments, rAAV particle compositions of higher than $10^{13}$ vgs/mL, for example higher than $10^{15}$ vgs/mL, are administered. In some embodiments, 0.0001 mL to 10 mLs are delivered to a subject (e.g., via one or more routes of administration as described in this application).

IV and IT injections are routine non-surgical procedures that are often done in an outpatient setting with minimal risk (Mattar, C. et al., FASEB J, 29(9):3876, 2015; Gray, S. et al., Gene Ther, 20(4):450-9, 2013; Federici, T. et al., Gene Ther, 19(8):852, 2012; Snyder, B. et al., Hum Gene Ther, 22(9): 1129, 2011).

The pharmaceutical forms of the rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The composition may include rAAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Subjects

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having Friedreich's ataxia. Friedreich's ataxia (FRDA) is a rare inherited disease that causes degeneration of the spinal cord and peripheral nervous system. Subjects with FRDA generally have an expanded number of GAA repeats in the FXN gene. A subject generally must have both copies of the FXN with expanded repeats to develop FRDA, although about 2 percent of subjects have one copy of the FXN gene with expanded repeats and another different type of mutation in the other copy of the FXN gene. Generally, if a subject has more than 66 to more than 1,000 GAA repeats in both copies of the FXN gene, they will develop FRDA. Symptoms of FRDA include gait ataxia, loss of sensation in the extremities, loss of tendon reflexes, scoliosis, dysarthria, hearing loss, vision loss, chest pain, shortness of breath, and heart palpitations. Subjects with FRDA may also develop carbohydrate intolerance or diabetes. Subjects with fewer than 300 repeats may develop symptoms later in life than those with additional repeats. Subject having FRDA can be identified by the skilled practitioner using methods known in the art or described herein, e.g., using genetic testing, electromyogram (EMG), nerve conduction studies, electrocardiogram (ECG), echocardiogram, blood tests for elevated glucose and vitamin E, magnetic resonance imaging (MRI) or computed tomography (CT) scans, and combinations thereof.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Frataxin: A Putative Biomarker for Minimal Effective Dosage of AAV Gene Therapy Friedrich ataxia (FRDA) is an autosomal recessive neurodegenerative disorder caused by a triplet repeat expansion in the frataxin gene (FXN), which encodes the mitochondrial protein frataxin. Deficiency in frataxin expression results in severe mitochondrial dysfunction leading to progressive gait abnormality, impaired muscle coordination, muscle weakness, hyporeflexia, dysmetria, dysarthria, and hypertrophic cardiomyopathy. Currently, there are no approved treatments for FRDA, which is the most common occurring autosomal recessive ataxia, affecting 1 in 50,000 people worldwide. Precise quantification of frataxin levels is critical for establishing the effectiveness of potential therapies. Therefore, methods that improve detection of FXN expression will facilitate the implementation of novel therapies into a clinical setting. The overall objective was to establish an approach for effective gene transfer and quantification of frataxin levels sufficient to restore mitochondrial function. Stable isotope labeling of amino acids in cell culture or in mammals (SILAC/M) is a novel and sensitive mass spectrometry based approach used herein for the quantification of frataxin levels; therefore enabling determination of required levels for correction of FXN deficiency.

Figure 6:
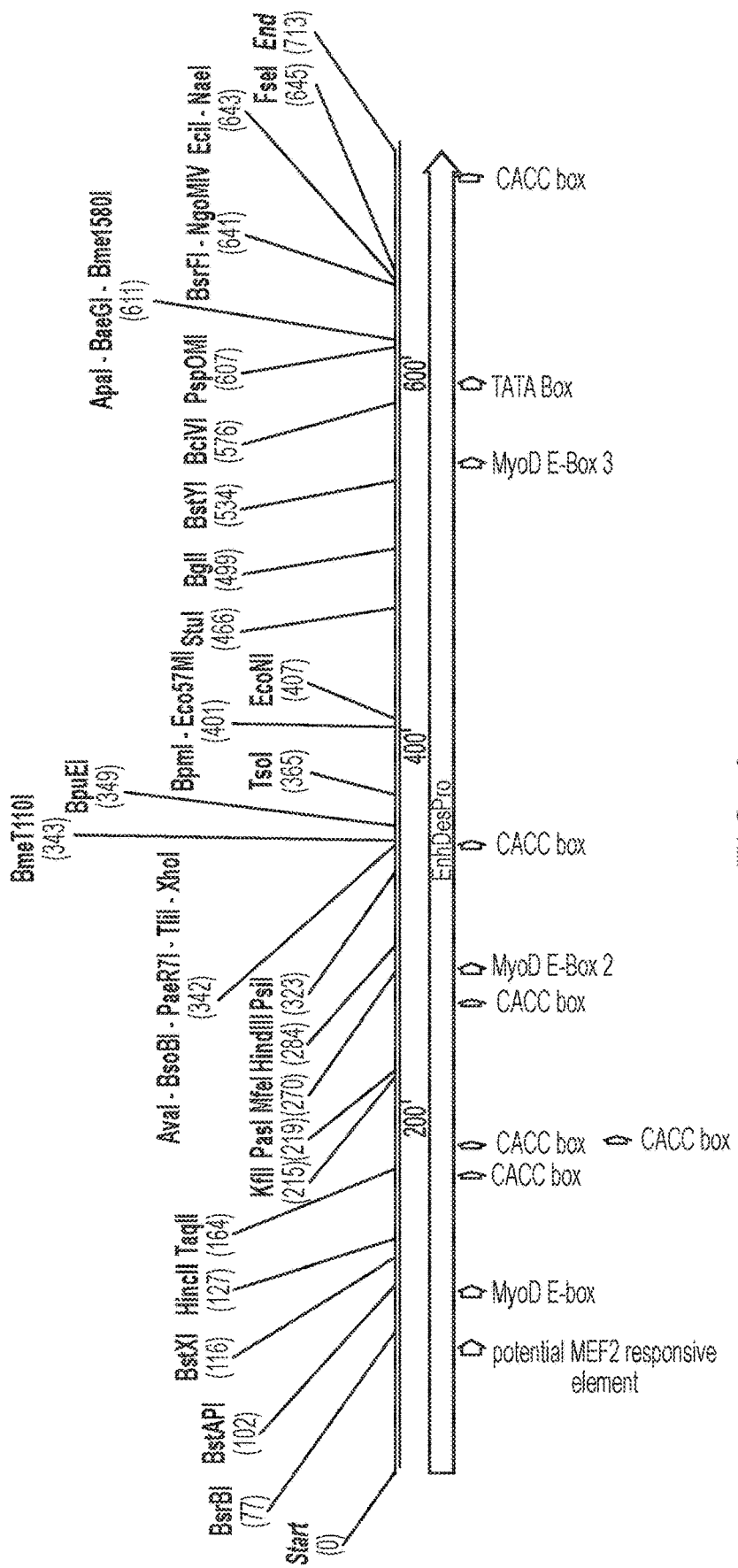
FIG. 6 shows an exemplary map of a Desmin promoter.

A rAAV2/9-FXN vector expressing codon optimized human FXN was generated for use in models of FRDA. rAAV2/9 means that the nucleic acid vector contained AAV2 ITRs and the capsid encapsidating the nucleic acid vector was an AAV9 capsid. A map of a non-limiting plasmid containing the FXN expression construct is shown in FIG. 1. The sequence of the plasmid is below. The sequence of the Desmin promoter in the plasmid is also shown (SEQ ID NO: 2, and see also FIG. 6). The frataxin gene sequence was codon-optimized using LifeTechnologies strategy using GeneOptimizer® software which calculates the optimal DNA sequence needed to encode the protein of interest (gene optimization).

AAV Plasmid with Human FXN Codon-Optimized Coding Sequence and Truncated 3' UTR Driven by Desmin Promoter (ITR from Position 22-164, Desmin Promoter from Position 171-882, SD/SA. From Position 896-1026, CDS (Codon Optimized Human Frataxin—hFXNco) from Position 1087-2034, 3' UTR (Human FXN 3' UTR) from Position 2035-3525, polyA Signal from Position 3550-3771, and ITR (Complement) from Position 3792-3934):

```
                                                          (SEQ ID NO: 10)
   1 CTGCAGGGGG GGGGGGGGGG GGGTTGGCCA CTCCCTCTCT GCGCGCTCGC TCGCTCACTG

61 AGGCCGGGCG ACCAAAGGTC GCCCGACGCC CGGGCTTTGC CCGGGCGGCC TCAGTGAGCG

121 AGGGAGCGCG CAGAGAGGGA GTGGCCAACT CCATCACTAG GGGTTCCTCA GATCTTACCC

181 CCTGCCCCCC ACAGCTCCTC TCCTGTGCCT TGTTTCCCAG CCATGCGTTC TCCTCTATAA

241 ATACCCGCTC TGGTATTTGG GGTTGGCAGC TGTTGCTGCC AGGGAGATGG TTGGGTTGAC

301 ATGCGGCTCC TGACAAAACA CAAACCCCTG GTGTGTGTGG GCGTGGGTGG TGTGAGTAGG

361 GGGATGAATC AGGGAGGGGG CGGGGGACCC AGGGGGCAGG AGCCACACAA AGTCTGTGCG

421 GGGGTGGGAG CGCACATAGC AATTGGAAAC TGAAAGCTTA TCAGACCCTT TCTGGAAATC

481 AGCCCACTGT TTATAAACTT GAGGCCCCAC CCTCGAGATA ACCAGGGCTG AAAGAGGCCC

541 GCCTGGGGGG TGGAGACATG CTTGCTGCCT GCCCTGGCGA AGGATTGGCA GGCTTGCCCG

601 TCACAGGACC CCCGCTGGCT GACTCAGGGG CGCAGGCCTC TTGCGGGGGA GCTGGCCTCC

661 CCGCCCCCAC GGCCACGGGC CGCCCTTTCC TGGCAGGACA GCGGGATCTT GCAGCTGTCA

721 GGGGAGGGGA GGCGGGGGCT GATGTCAGGA GGGATACAAA TAGTGCCGAC GGCTGGGGGC

781 CCTGTCTCCC CTCGCCGCAT CCACTCTCCG GCCGGCCGCC TGTCCGCCGC CTCCTCCGTG

841 CGCCCGCCAG CCTCGCCCGC GCCGTCACCG TGAGGCACTG GGCAGGTAAG TATCAAAGTA

901 TCAAGGTTAC AAGACAGGTT TAAGGAGACC AATAGAAATT GGGCTTGTCG AGACAGAGAA

961 GACTCTTGCG TTTCTGATAG GCACCTATTG GTCTTACTGA CATCCACTTT GCCTTTCTCT

1021 CCACAGGCTA GCCTCGAGAA TTCACGCGTG GTACCTCTAG AGTCGACCGA TATCACTAGT

1081 GCCACCATGT GGACACTGGG GAGAAGGGCC GTGGCTGGAC TGCTGGCTTC TCCATCTCCA

1141 GCCCAGGCCC AGACCCTGAC CAGAGTGCCT AGACCTGCCG AACTGGCCCC TCTGTGTGGC

1201 AGAAGAGGCC TGAGAACCGA CATCGACGCC ACCTGTACCC CCAGAAGGGC CAGCAGCAAT

1261 CAGCGGGGCC TGAATCAGAT CTGGAACGTG AAGAAACAGA GCGTGTACCT GATGAACCTG

1321 AGAAAGAGCG GCACCCTGGG CCACCCTGGA AGCCTGGATG AGACAACCTA CGAGCGGCTG

1381 GCCGAGGAAA CCCTGGATTC CCTGGCCGAG TTCTTCGAGG ACCTGGCCGA CAAGCCCTAC

1441 ACCTTCGAGG ATTACGACGT GTCCTTCGGC AGCGGCGTGC TGACAGTGAA GCTGGGCGGA
```

```
-continued

1501  GATCTGGGCA CCTACGTGAT CAACAAGCAG ACCCCCAACA AACAGATCTG GCTGAGCAGC
1561  CCCAGCAGCG GCCCCAAGAG ATACGATTGG ACCGGCAAGA ACTGGGTGTT CAGCCACGAC
1621  GGCGTGTCCC TGCATGAGCT GCTGGCTGCC GAGCTGACCA AGGCCCTGAA AACAAAGCTG
1681  GACCTGAGCT GGCTGGCCTA CAGCGGCAAA GATGCCATCG ATATCCCCAG CCCCGTTTTA
1741  AGGACATTAA AAGCTATCAG GCCAAGACCC CAGCTTCATT ATGCAGCTGA GGTCTGTTTT
1801  TTGTTGTTGT TGTTGTTTAT TTTTTTTATT CCTGCTTTTG AGGACAGTTG GGCTATGTGT
1861  CACAGCTCTG TAGAAAGAAT GTGTTGCCTC CTACCTTGCC CCCAAGTTCT GATTTTTAAT
1921  TTCTATGGAA GATTTTTTGG ATTGTCGGAT TTCCTCCCTC ACATGATACC CCTTATCTTT
1981  TATAATGTCT TATGCCTATA CCTGAATATA CAACCTTTA AAAAGCAAA ATAATAAGAA
2041  GGAAAAATTC CAGGAGGGAA AATGAATTGT CTTCACTCTT CATTCTTTGA AGGATTTACT
2101  GCAAGAAGTA CATGAAGAGC AGCTGGTCAA CCTGCTCACT GTTCTATCTC CAAATGAGAC
2161  ACATTAAAGG GTAGCCTACA AATGTTTTCA GGCTTCTTTC AAAGTGTAAG CACTTCTGAG
2221  CTCTTTAGCA TTGAAGTGTC GAAAGCAACT CACACGGGAA GATCATTTCT TATTTGTGCT
2281  CTGTGACTGC CAAGGTGTGG CCTGCACTGG GTTGTCCAGG GAGACATGCA TCTAGTGCTG
2341  TTTCTCCCAC ATATTCACAT ACGTGTCTGT GTGTATATAT ATTTTTTCAA TTTAAAGGTT
2401  AGTATGGAAT CAGCTGCTAC AAGAATGCAA AAATCTTCC AAAGACAAGA AAGAGGAAA
2461  AAAAGCCGTT TTCATGAGCT GAGTGATGTA GCGTAACAAA CAAAATCATG GAGCTGAGGA
2521  GGTGCCTTGT AAACATGAAG GGGCAGATAA AGGAAGGAGA TACTCATGTT GATAAAGAGA
2581  GCCCTGGTCC TAGACATAGT TCAGCCACAA AGTAGTTGTC CCTTTGTGGA CAAGTTTCCC
2641  AAATTCCCTG GACCTCTGCT TCCCCATCTG TTAAATGAGA GAATAGAGTA TGGTTGATTC
2701  CCAGCATTCA GTGGTCCTGT CAAGCAACCT AACAGGCTAG TTCTAATTCC CTATTGGGTA
2761  GATGAGGGGA TGACAAAGAA CAGTTTTTAA GCTATATAGG AAACATTGTT ATTGGTGTTG
2821  CCCTATCGTG ATTTCAGTTG AATTCATGTG AAAATAATAG CCATCCTTGG CCTGGCGCGG
2881  TGGCTCACAC CTGTAATCCC AGCACTTTTG GAGGCCAAGG TGGGTGGATC ACCTGAGGTC
2941  AGGAGTTCAA GACCAGCCTG GCCAACATGA TGAAACCCCG TCTCTACTAA AATACAAAA
3001  AATTAGCCGG GCATGATGGC AGGTGCCTGT AATCCCAGCT ACTTGGGAGG CTGAAGCGGC
3061  AGAATCGCTT GAACCCAGAG GTGGAGGTTG CAGTGAGCCG AGATCGTGCC ATTGCACTGT
3121  AACCTGGGTG ACTGAGCAAA ACTCTGTCTC AAAATAATAA TAACAATATA ATAATAATAA
3181  TAGCCATCCT TTATTGTACC CTTACTGGGT TAATCGTATT ATACCACATT ACCTCATTTT
3241  AATTTTTACT GACCTGCACT TTATACAAAG CAACAAGCCT CCAGGACATT AAAATTCATG
3301  CAAAGTTATG CTCATGTTAT ATTATTTTCT TACTTAAAGA AGGATTTATT AGTGGGTGGG
3361  CATGGTGGCG TGCACCTGTA ATCCCAGGTA CTCAGGAGGC TGAGACGGGA GAATTGCTTG
3421  ACCCCAGGCG GAGGAGGTTA CAGTGAGTCG AGATCGTACC TGAGCGACAG AGCGAGACTC
3481  CGTCTCAAAA AAAAAAAAA GGAGGGTTTA TTAATGAGAA GTTTGGTCGA CTAGAGCGGC
3541  CGCTTCGAGC AGACATGATA AGATACATTG ATGAGTTTGG ACAAACCACA ACTAGAATGC
3601  AGTGAAAAA ATGCTTTATT TGTGAAATTT GTGATGCTAT TGCTTTATTT GTAACCATTA
3661  TAAGCTGCAA TAAACAAGTT AACAACAACA ATTGCATTCA TTTTATGTTT CAGGTTCAGG
3721  GGGAGATGTG GGAGGTTTTT TAAAGCAAGT AAAACCTCTA CAAATGTGGT AAAATCGATA
3781  AGGATCTAGG AACCCCTAGT GATGGAGTTG GCCACTCCCT CTCTGCGCGC TCGCTCGCTC
3841  ACTGAGGCCG CCCGGGCAAA GCCCGGGCGT CGGGCGACCT TTGGTCGCCC GGCCTCAGTG
```

-continued

```
3901 AGCGAGCGAG CGCGCAGAGA GGGAGTGGCC AACCCCCCCC CCCCCCCCCC TGCAGCCTGG

3961 CGTAATAGCG AAGAGGCCCG CACCGATCGC CCTTCCCAAC AGTTGCGTAG CCTGAATGGC

4021 GAATGGCGCG ACGCGCCCTG TAGCGGCGCA TTAAGCGCGG CGGGTGTGGT GGTTACGCGC

4081 AGCGTGACCG CTACACTTGC CAGCGCCCTA GCGCCCGCTC CTTTCGCTTT CTTCCCTTCC

4141 TTTCTCGCCA CGTTCGCCGG CTTTCCCCGT CAAGCTCTAA ATCGGGGCT CCCTTTAGGG

4201 TTCCGATTTA GTGCTTTACG GCACCTCGAC CCCAAAAAAC TTGATTAGGG TGATGGTTCA

4261 CGTAGTGGGC CATCGCCCTG ATAGACGGTT TTTCGCCCTT TGACGTTGGA GTCCACGTTC

4321 TTTAATAGTG GACTCTTGTT CCAAACTGGA ACAACACTCA ACCCTATCTC GGTCTATTCT

4381 TTTGATTTAT AAGGGATTTT GCCGATTTCG GCCTATTGGT TAAAAAATGA GCTGATTTAA

4441 CAAAAATTTA ACGCGAATTT TAACAAAATA TTAACGTTTA CAATTTCCTG ATGCGGTATT

4501 TTCTCCTTAC GCATCTGTGC GGTATTTCAC ACCGCATATG GTGCACTCTC AGTACAATCT

4561 GCTCTGATGC CGCATAGTTA AGCCAGCCCC GACACCCGCC AACACCCGCT GACGCGCCCT

4621 GACGGGCTTG TCTGCTCCCG GCATCCGCTT ACAGACAAGC TGTGACCGTC TCCGGGAGCT

4681 GCATGTGTCA GAGGTTTTCA CCGTCATCAC CGAAACGCGC GAGACGAAAG GCCTCGTGA

4741 TACGCCTATT TTTATAGGTT AATGTCATGA TAATAATGGT TTCTTAGACG TCAGGTGGCA

4801 CTTTTCGGGG AAATGTGCGC GGAACCCCTA TTTGTTTATT TTTCTAAATA CATTCAAATA

4861 TGTATCCGCT CATGAGACAA TAACCCTGAT AAATGCTTCA ATAATATTGA AAAGGAAGA

4921 GTATGAGTAT TCAACATTTC CGTGTCGCCC TTATTCCCTT TTTTGCGGCA TTTTGCCTTC

4981 CTGTTTTTGC TCACCCAGAA ACGCTGGTGA AAGTAAAAGA TGCTGAAGAT CAGTTGGGTG

5041 CACGAGTGGG TTACATCGAA CTGGATCTCA ACAGCGGTAA GATCCTTGAG AGTTTTCGCC

5101 CCGAAGAACG TTTTCCAATG ATGAGCACTT TTAAAGTTCT GCTATGTGGC GCGGTATTAT

5161 CCCGTATTGA CGCCGGGCAA GAGCAACTCG GTCGCCGCAT ACACTATTCT CAGAATGACT

5221 TGGTTGAGTA CTCACCAGTC ACAGAAAAGC ATCTTACGGA TGGCATGACA GTAAGAGAAT

5281 TATGCAGTGC TGCCATAACC ATGAGTGATA ACACTGCGGC CAACTTACTT CTGACAACGA

5341 TCGGAGGACC GAAGGAGCTA ACCGCTTTTT TGCACAACAT GGGGGATCAT GTAACTCGCC

5401 TTGATCGTTG GGAACCGGAG CTGAATGAAG CCATACCAAA CGACGAGCGT GACACCACGA

5461 TGCCTGTAGC AATGGCAACA ACGTTGCGCA AACTATTAAC TGGCGAACTA CTTACTCTAC

5521 CTTCCCGGCA ACAATTAATA GACTGGATGG AGGCGGATAA AGTTGCAGGA CCACTTCTGC

5581 GCTCGGCCCT TCCGGCTGGC TGGTTTATTG CTGATAAATC TGGAGCCGGT GAGCGTGGGT

5641 CTCGCGGTAT CATTGCAGCA CTGGGGCCAG ATGGTAAGCC CTCCCGTATC GTAGTTATCT

5701 ACACGACGGG GAGTCAGGCA ACTATGGATG AACGAAATAG ACAGATCGCT GAGATAGGTG

5761 CCTCACTGAT TAAGCATTGG TAACTGTCAG ACCAAGTTTA CTCATATATA CTTTAGATTG

5821 ATTTAAAACT TCATTTTTAA TTTAAAAGGA TCTAGGTGAA GATCCTTTTT GATAATCTCA

5881 TGACCAAAAT CCCTTAACGT GAGTTTTCGT TCCACTGAGC GTCAGACCCC GTAGAAAAGA

5941 TCAAAGGATC TTCTTGAGAT CCTTTTTTTC TGCGCGTAAT CTGCTGCTTG CAAACAAAAA

6001 AACCACCGCT ACCAGCGGTG GTTTGTTTGC CGGATCAAGA GCTACCAACT CTTTTTCCGA

6061 AGGTAACTGG CTTCAGCAGA GCGCAGATAC CAAATACTGT CCTTCTAGTG TAGCCGTAGT

6121 TAGGCCACCA CTTCAAGAAC TCTGTAGCAC CGCCTACATA CCTCGCTCTG CTAATCCTGT

6181 TACCAGTGGC TGCTGCCAGT GGCGATAAGT CGTGTCTTAC CGGGTTGGAC TCAAGACGAT

6241 AGTTACCGGA TAAGGCGCAG CGGTCGGGCT GAACGGGGGG TTCGTGCACA CAGCCCAGCT

6301 TGGAGCGAAC GACCTACACC GAACTGAGAT ACCTACAGCG TGAGCATTGA GAAAGCGCCA
```

```
6361 CGCTTCCCGA AGGGAGAAAG GCGGACAGGT ATCCGGTAAG CGGCAGGGTC GGAACAGGAG

6421 AGCGCACGAG GGAGCTTCCA GGGGGAAACG CCTGGTATCT TTATAGTCCT GTCGGGTTTC

6481 GCCACCTCTG ACTTGAGCGT CGATTTTTGT GATGCTCGTC AGGGGGGCGG AGCCTATGGA

6541 AAAACGCCAG CAACGCGGCC TTTTTACGGT TCCTGGCCTT TTGCTGGCCT TTTGCTCACA

6601 TGTTCTTTCC TGCGTTATCC CCTGATTCTG TGGATAACCG TATTACCGCC TTTGAGTGAG

6661 CTGATACCGC TCGCCGCAGC CGAACGACCG AGCGCAGCGA GTCAGTGAGC GAGGAAGCGG

6721 AAGAGCGCCC AATACGCAAA CCGCCTCTCC CCGCGCGTTG GCCGATTCAT TAATGCAGGG
```

A polypeptide translation is as follows:

(SEQ ID NO: 11)
MWTLGRRAVAGLLASPSPAQATLTRVPRPAELAPLCGRRGLRTDIDATCT

PRRASSNQRGLNQTWNVKKQSVYLMNLRKSGTLGHPGSLDETTYERLAEE

TLDSLAEFFEDLADKPYTFEDYDVSFGSGVLTVKLGGDLGTYVINKQTPN

KQIWLSSPSSGPKRYDWTGKNWVFSHDGVSLHELLAAELTKALKTKLDLS

WLAYSGKDAIDIPSPVLRTLKAIRPRPQLHYAAEVCFLLLLLFIFFIPAF

EDSWAMCHSSVERMCCLLPCPQVLIFNFYGRFFGLSDFLPHMIPLIFYNV

LCLYLNITTFKKAK

Renal epithelial cells (REC) were isolated from control and FRDA patients, and SILAC was used to quantify AAV-mediated FXN expression in-vitro. Induced pluripotent stem cells (MSC) were generated from the RECs, and were subsequently differentiated to cardiomyocytes and neurons. AAV-mediated correction of FXN was verified by increased mitochondrial activity including reduced iron deposition and increased aconitase function in FRDA cells. Preliminary results showed that SILAC/M was able to accurately measure endogenous and vector derived FXN expression in-vitro and in-vivo. Moreover, improvement in mitochondrial function was correlated with levels of FXN expression in vitro. These studies indicate that rAAV vectors of the present disclosure are useful to treat FRDA.

Example 2: Development of an AAV Vector to Treat Friedreich's Ataxia

A clinical candidate vector was designed to express frataxin. The vector contained an expression cassette with human Desmin (DES) promoter driving codon-optimized human FXN with a truncated human FXN 3' UTR. The expression cassette was flanked by AAV2 ITRs. The plasmid containing the expression cassette is shown in FIG. 1 and is further described in Example 1. The plasmid was used with AAV2 rep and AAV9 capsid helper plasmids to package the vector in an AAV9 capsid, resulting in rAAV2/9-FXN, which was used in all of the studies described below.

Figures 2A, 2B, 2C:
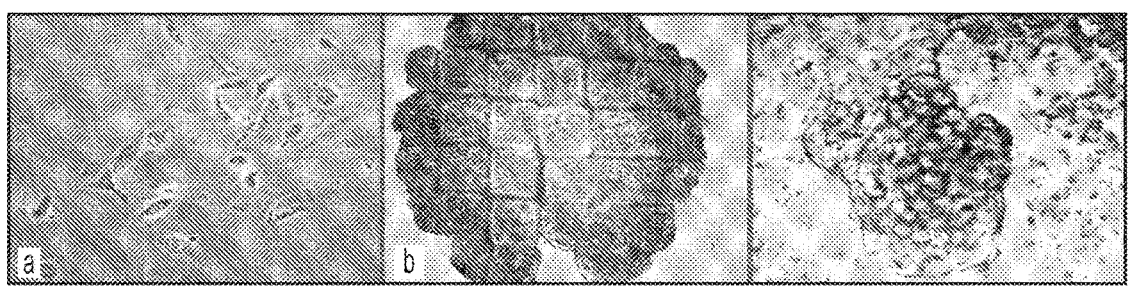
FIG. 2A shows an exemplary photograph of renal epithelial cells (REC) isolated from FRDA patients.
FIG. 2B shows an exemplary photograph of induced pluripotent stem cells (IPSCs) generated from the RECs.
FIG. 2C shows a photograph of a contracting cardiomyocyte generated from the IPSCs.

A cellular model of FRDA was developed as follows. FA2 cells are renal epithelial cells that were derived from FRDA patients (FIG. 2A). Induced pluripotent stem cells (IPSCs) were generated from the FA2 cells (FIG. 2B) and were differentiated into cardiomyocytes (FIG. 2C) and neural progenitor cells. Cardiomyocyte differentiation took about two weeks, whereas neural progenitor cell differentiation took about three weeks.

Figure 3A:
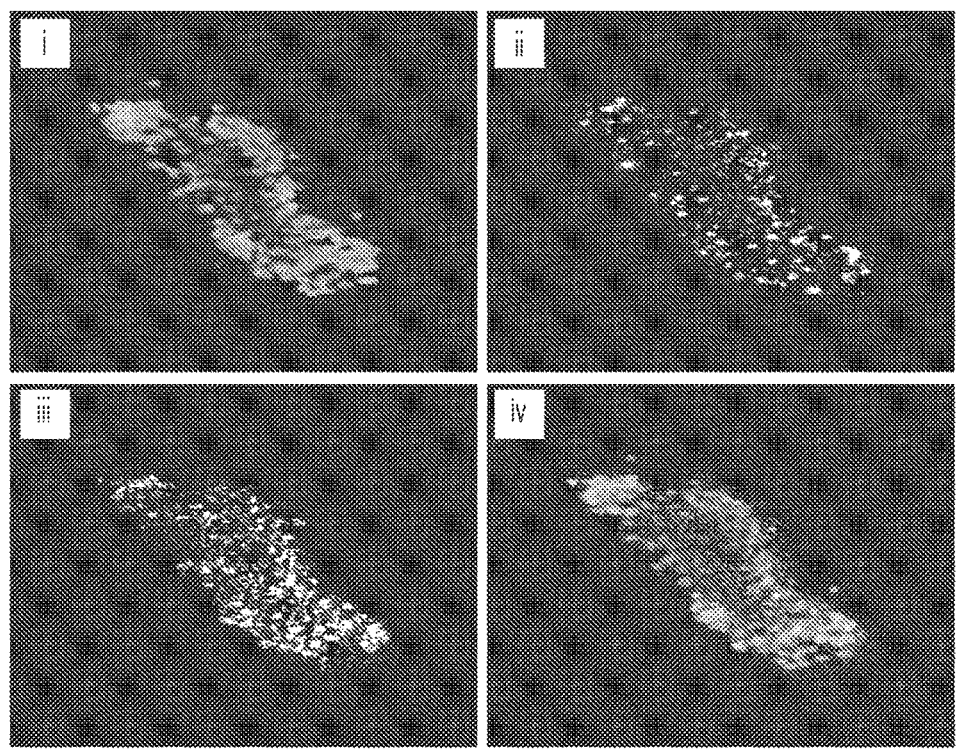
FIG. 3A shows a series of exemplary photographs of cardiomyocytes generated from the IPSCs stained with different markers. (i) shows DAPI staining, (ii) shows NKX2.5 staining, (iii) shows TroponinT staining, and (iv) shows an overlay of (i)-(iii).
Figure 3B:
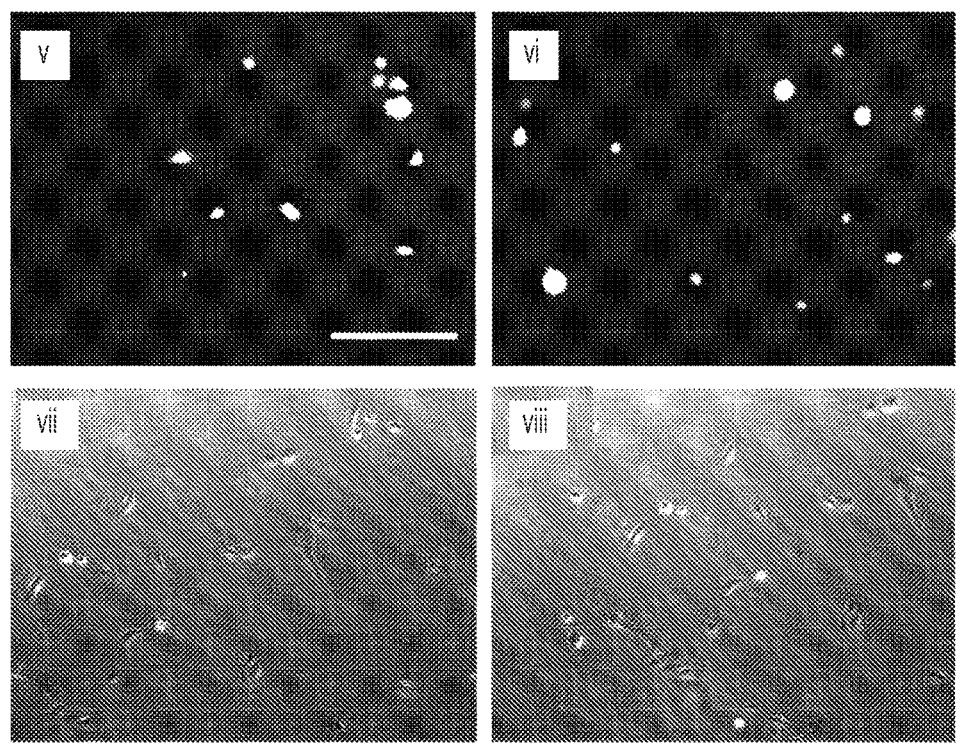
FIG. 3B shows a series of exemplary photographs of neural progenitor cells (NPCs) generated from the IPSCs stained with different markers. (v) and (vi) show staining with Neurofluor CDr3 and Hoechst dye 33258. (vii) and (viii) show phase images of NPC cell morphology.

The IPSC differentiation to cardiomyocytes and progenitor cells was validated by assessing cardiac and neuronal markers. NKX2.5 and TroponinT were used as markers of cardiomyocytes. The IPSCs differentiated into cardiomyocytes expressed both markers (FIG. 3A). Neurofluor CDr3 was used to confirm neural progenitor cell differentiation. The IPSCs differentiated into neural progenitors stained positive with Neurofluor CDr3 (FIG. 3B).

Figure 4:
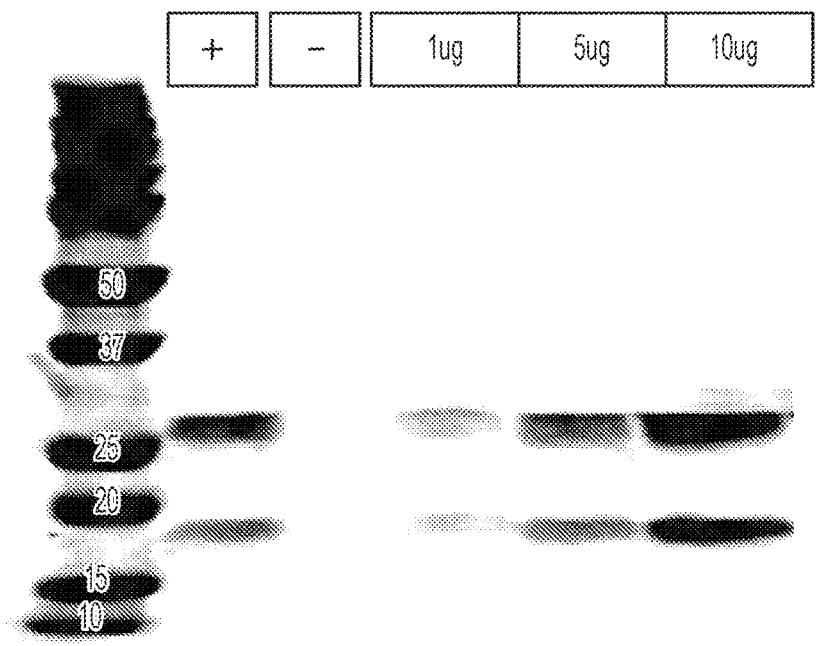
FIG. 4 shows an image of an exemplary Western blot stained with an anti-frataxin antibody. "+" is FA2 cells transiently transfected with the FXN expression plasmid. "−" is FA2 cells that are not transfected. 1 ug, 5 ug, and 10 ug are amounts of purified FXN.

Next, FA2 cells were transiently transfected with the plasmid containing the FXN expression construct and FXN protein levels were analyzed by Western Blot and the Li-COR Odyssey Imaging system. FA2 transiently transfected cells showing dose dependent increases of FXN (FIG. 4).

Figure 5A:
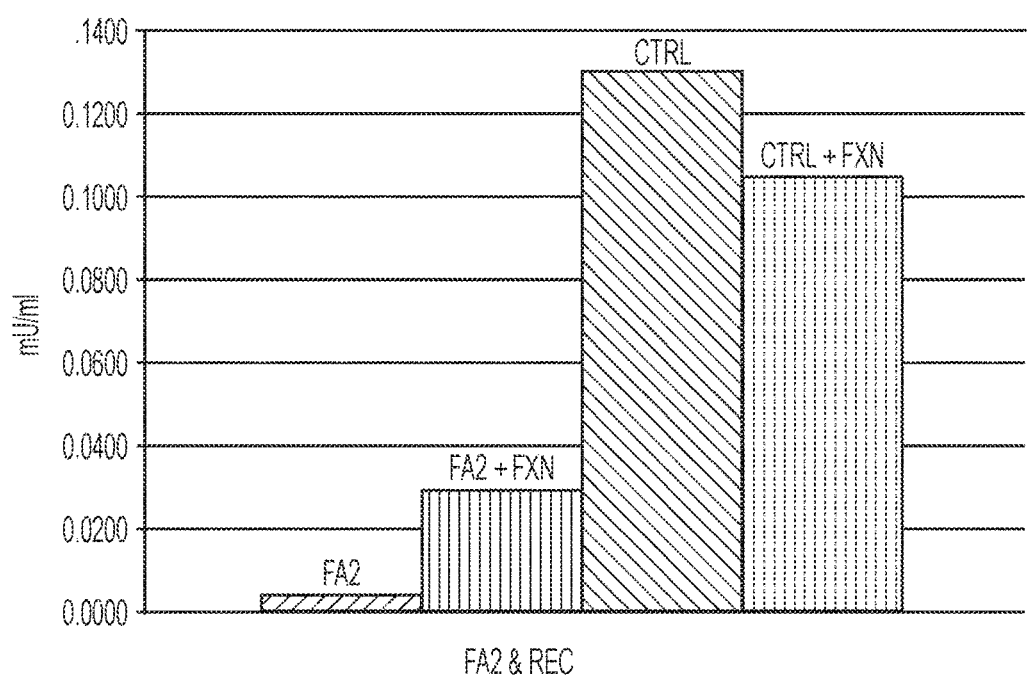
FIG. 5A shows exemplary aconitase activity in FRDA patient-derived cells. FA2=untreated FRDA cells, FA2+FXN=FRDA cells transiently transfected with the FXN expression plasmid, CTRL=Healthy control cells; CTRL+FXN=healthy control cells transiently transfected with the FXN expression plasmid.
Figure 5B:
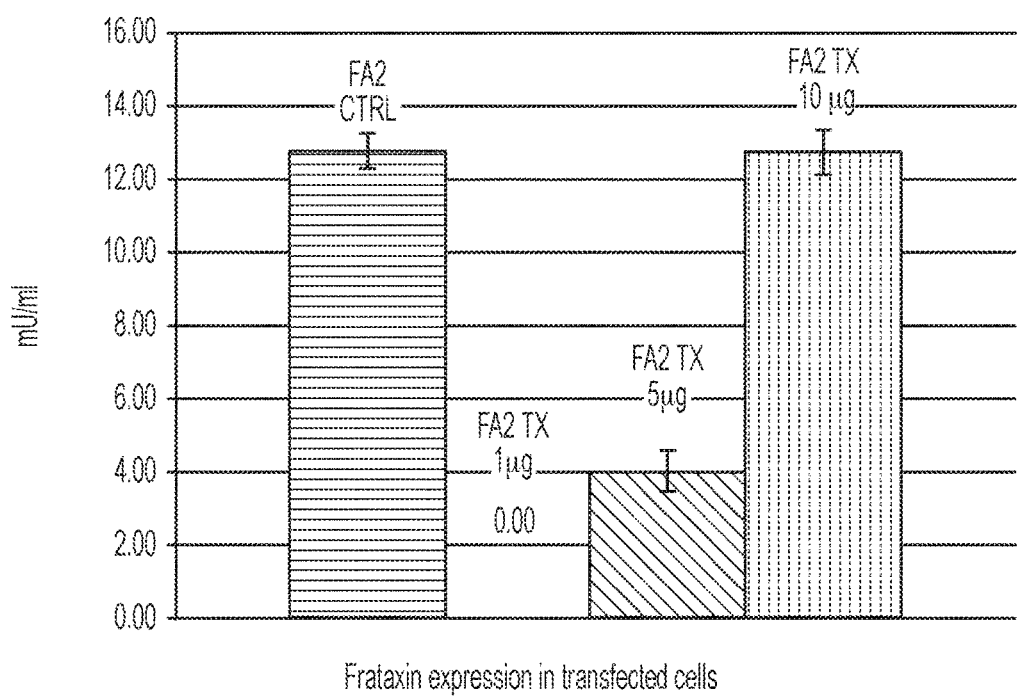
FIG. 5B shows exemplary aconitase activity in FRDA patient-derived cells. FA2 CTRL=FRDA cell without transfection, FA2 TX 1 µg=FRDA cells transfected with 1 µg of plasmid, FA2 TX 5 µg=FRDA cells transfected with 5 µg of plasmid, FA2 TX 10 µg=FRDA cells transfected with 10 µg of plasmid.

Lastly, an aconitase activity assay was used to assess mitochondrial health in FA2 cells. Aconitase is a robust indicator of mitochondrial health. Moreover, in FXN deficient environments aconitase becomes susceptible to ROS attack. FA2 cells were transiently transfected with the plasmid containing the FXN expression construct. Aconitase activity was higher in FA2 cells transfected with the plasmid than in FA2 cells not transfected with the plasmid (FIGS. 5A and 5B).

These results show that correction of FXN expression in-vitro increased aconitase activity. Aconitase activity increased proportionally to FXN in a dose dependent manner. Western Blot analysis revealed that the expression vector generated transcriptionally and functionally active FXN. These results suggest that rAAV compositions of the present disclosure are useful, in some embodiments, for AAV-mediated gene therapy for FXN replacement in Friedreich's Ataxia.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A nucleic acid comprising an expression construct comprising a human frataxin (FXN) coding sequence and a truncated human FXN 3' untranslated region (UTR) operably linked to a promoter, wherein the expression construct is flanked on each side by an inverted terminal repeat sequence,
   wherein the FXN 3' UTR is truncated relative to the wild-type FXN 3' UTR sequence of SEQ ID NO: 9,
   wherein the FXN coding sequence is codon-optimized for expression in human cells, and
   wherein the FXN coding sequence is at least 90% identical to a sequence within SEQ ID NO: 1 that encodes a 210 amino acid human FXN protein.

2. The nucleic acid of claim 1, wherein the promoter comprises one or more of the following, or a fragment or variant thereof: a Desmin promoter, a chicken (β-actin (CBA) promoter, or an endogenous human FXN promoter (hFXNPro).

3. The nucleic acid of claim 1, wherein the truncated human FXN 3' UTR comprises the sequence of SEQ ID NO: 3.

4. The nucleic acid of claim 1, wherein the nucleic acid is a recombinant adeno-associated virus (rAAV) vector.

5. The nucleic acid of claim 4, wherein the nucleic acid is a single-stranded or self-complementary rAAV nucleic acid vector.

6. A recombinant adeno-associated virus (rAAV) particle comprising the nucleic acid of claim 4.

7. The rAAV particle of claim 6, wherein the rAAV particle is an AAV9 particle.

8. A composition comprising a plurality of the rAAV particle of claim 6.

9. The composition of claim 8 further comprising a pharmaceutically acceptable carrier.

10. A method of treating Friedreich's ataxia, the method comprising administering a therapeutically effective amount of the rAAV particle of claim 6 to a subject having Friedreich's ataxia.

11. The method of claim 10, wherein the rAAV particle is administered via intravenous injection.

12. The method of claim 10, wherein the rAAV particle is administered via intrathecal injection.

13. The method of claim 10, wherein the rAAV particle is administered via intracisternal injection.

14. The method of claim 11 further comprising administering the rAAV particle via intrathecal injection.

15. The method of claim 11 further comprising administering the rAAV particle via intracisternal injection.

16. The method of claim 14, wherein the ratio of rAAV particle administered to the subject via intravenous injection to rAAV particle administered to the subject via intrathecal injection is 1:10.

17. The method of claim 15, wherein the ratio of rAAV particle administered to the subject via intravenous injection to rAAV particle administered to the subject via intracisternal injection is 1:10.

18. The nucleic acid of claim 1, wherein the truncated human FXN 3' UTR is at least 100 nucleotides shorter than the wild-type FXN 3' UTR of SEQ ID NO: 9.

19. The nucleic acid of claim 18, wherein the truncated FXN 3' UTR sequence has at least 85% sequence identity with the corresponding sequence in the wild-type FXN 3' UTR of SEQ ID NO: 9.

20. The nucleic acid of claim 1, wherein the truncated human FXN 3' UTR is between 500 and 800 nucleotides shorter than the wild-type FXN 3' UTR of SEQ ID NO: 9.

21. A nucleic acid comprising an expression construct comprising a codon-optimized human frataxin (FXN) coding sequence and a truncated human FXN 3' untranslated region (UTR) operably linked to a promoter, wherein the expression construct is flanked on each side by an inverted terminal repeat sequence,
   wherein the FXN coding sequence is codon-optimized for expression in human cells, and
   wherein the wild-type FXN 3' UTR comprises a nucleic acid sequence of SEQ ID NO: 3 and is no more than 2000 nucleotides in length.

22. A nucleic acid comprising an expression construct comprising a codon-optimized human frataxin (FXN) coding sequence, wherein the expression construct is flanked on each side by an inverted terminal repeat sequence, wherein the FXN coding sequence is codon-optimized for expression in human cells, and wherein the FXN coding sequence is at least 90% identical to a sequence within SEQ ID NO: 1 that encodes a 210 amino acid human FXN protein.

* * * * *

SEQUENCE LISTING

<160> NUMBER OF SEQ ID NOS: 11

<210> SEQ ID NO 1
<211> LENGTH: 948
<212> TYPE: DNA
<213> ORGANISM: Artificial Sequence
<220> FEATURE:
<223> OTHER INFORMATION: Synthetic Polynucleotide

<400> SEQUENCE: 1

```
atgtggacac tggggagaag ggccgtggct ggactgctgg cttctccatc tccagcccag      60
gcccagaccc tgaccagagt gcctagacct gccgaactgg cccctctgtg tggcagaaga     120
ggcctgagaa ccgacatcga cgccacctgt acccccagaa gggccagcag caatcagcgg     180
ggcctgaatc agatctggaa cgtgaagaaa cagagcgtgt acctgatgaa cctgagaaag     240
agcggcaccc tgggccaccc tggaagcctg gatgagacaa cctacgagcg gctggccgag     300
gaaaccctgg attccctggc cgagttcttc gaggacctgg ccgacaagcc ctacaccttc     360
gaggattacg acgtgtcctt cggcagcggc gtgctgacag tgaagctggg cggagatctg     420
ggcacctacg tgatcaacaa gcagaccccc aacaaacaga tctggctgag cagccccagc     480
agcggcccca agagatacga ttggaccggc aagaactggg tgttcagcca cgacggcgtg     540
tccctgcatg agctgctggc tgccgagctg accaaggccc tgaaaacaaa gctggacctg     600
agctggctgg cctacagcgg caaagatgcc atcgatatcc ccagcccgt tttaaggaca      660
ttaaaagcta tcaggccaag accccagctt cattatgcag ctgaggtctg tttttttgttg     720
ttgttgttgt ttatttttt tattcctgct tttgaggaca gttgggctat gtgtcacagc     780
tctgtagaaa gaatgtgttg cctcctacct tgccccaag ttctgatttt taatttctat       840
ggaagatttt ttggattgtc ggatttcctc cctcacatga taccccttat cttttataat     900
gtcttatgcc tatacctgaa tataacaacc tttaaaaaag caaaataa                  948
```

<210> SEQ ID NO 2
<211> LENGTH: 712
<212> TYPE: DNA
<213> ORGANISM: Artificial Sequence
<220> FEATURE:
<223> OTHER INFORMATION: Synthetic Polynucleotide

<400> SEQUENCE: 2

```
gatcttaccc cctgccccc acagctcctc tcctgtgcct tgtttcccag ccatgcgttc       60
tcctctataa atacccgctc tggtatttgg ggttggcagc tgttgctgcc agggagatgg     120
ttgggttgac atgcggctcc tgacaaaaca caaaccccctg gtgtgtgtgg gcgtgggtgg    180
tgtgagtagg gggatgaatc agggaggggg cggggggaccc aggggggcagg agccacacaa  240
agtctgtgcg ggggtgggag cgcacatagc aattggaaac tgaaagctta tcagacccct    300
tctggaaatc agcccactgt ttataaactt gaggccccac cctcgagata accagggct     360
aaagaggccc gcctgggggc tggagacatg cttgctgcct gccctggcga aggattggca    420
ggcttgcccg tcacaggacc cccgctggct gactcagggg cgcaggcctc ttgcggggga    480
gctggcctcc ccgccccac ggccacgggc cgcccttcc tggcaggaca gcgggatctt      540
gcagctgtca ggggagggga ggcgggggct gatgtcagga gggatacaaa tagtgccgac    600
ggctgggggc cctgtctccc ctcgccgcat ccactctccg gccggccgcc tgtccgccgc    660
ctcctccgtg cgcccgccag cctcgcccgc gccgtcaccg tgaggcactg gg             712
```

<210> SEQ ID NO 3
<211> LENGTH: 1490
<212> TYPE: DNA
<213> ORGANISM: Artificial Sequence
<220> FEATURE:
<223> OTHER INFORMATION: Synthetic Polynucleotide

<400> SEQUENCE: 3

```
aagaaggaaa aattccagga gggaaaatga attgtcttca ctcttcattc tttgaaggat      60
ttactgcaag aagtacatga agagcagctg gtcaacctgc tcactgttct atctccaaat    120
gagacacatt aaagggtagc ctacaaatgt tttcaggctt ctttcaaagt gtaagcactt    180
ctgagctctt tagcattgaa gtgtcgaaag caactcacac gggaagatca tttcttattt    240
gtgctctgtg actgccaagg tgtggcctgc actgggttgt ccagggagac atgcatctag    300
tgctgtttct cccacatatt cacatacgtg tctgtgtgta tatatatttt ttcaatttaa    360
aggttagtat ggaatcagct gctacaagaa tgcaaaaaat cttccaaaga caagaaaaga    420
ggaaaaaaag ccgttttcat gagctgagtg atgtagcgta acaaacaaaa tcatggagct    480
gaggaggtgc cttgtaaaca tgaaggggca gataaaggaa ggagatactc atgttgataa    540
agagagccct ggtcctagac atagttcagc cacaaagtag ttgtcccttt gtggacaagt    600
ttcccaaatt ccctggacct ctgcttcccc atctgttaaa tgagagaata gagtatggtt    660
gattcccagc attcagtggt cctgtcaagc aacctaacag gctagttcta attcccgtatt    720
gggtagatga ggggatgaca agaacagtt tttaagctat ataggaaaca ttgttattgg    780
tgttgcccta tcgtgatttc agttgaattc atgtgaaaat aatagccatc cttggcctgg    840
cgcggtggct cacacctgta atcccagcac ttttggaggc caaggtgggt ggatcacctg    900
aggtcaggag ttcaagacca gcctggccaa catgatgaaa ccccgtctct actaaaaata    960
caaaaaatta gccgggcatg atggcaggtg cctgtaatcc cagctacttg ggaggctgaa   1020
gcggaagaat cgcttgaacc cagaggtgga ggttgcagtg agccgagatc gtgccattgc   1080
actgtaacct gggtgactga gcaaaactct gtctcaaaat aataataaca atataataat   1140
aataatagcc atccttttatt gtaccttac tgggttaatc gtattataacc acattacctc   1200
atttttaattt ttactgacct gcactttata caaagcaaca agcctccagg acattaaaat   1260
tcatgcaaag ttatgctcat gttatattat tttcttactt aaagaaggat ttattagtgg   1320
ctgggcatgg tggcgtgcac ctgtaatccc aggtactcag gaggctgaga cgggagaatt   1380
gcttgaccccc aggcggagga ggttacagtg agtcgagatc gtacctgagc gacagagcga   1440
gactccgtct caaaaaaaaa aaaaggagg gtttattaat gagaagtttg   1490
```

<210> SEQ ID NO 4
<211> LENGTH: 3601
<212> TYPE: DNA
<213> ORGANISM: Artificial Sequence
<220> FEATURE:
<223> OTHER INFORMATION: Synthetic Polynucleotide

<400> SEQUENCE: 4

```
gatcttaccc cctgccccc acagctcctc tcctgtgcct tgtttcccag ccatgcgttc       60
tcctctataa atacccgctc tggtatttgg ggttggcagc tgttgctgcc agggagatgg    120
ttgggttgac atgcggctcc tgacaaaaca caaaccctg gtgtgtgtgg gcgtgggtgg     180
tgtgagtagg gggatgaatc agggaggggg cgggggaccc aggggcagg agccacacaa    240
agtctgtgcg ggggtgggag cgcacatagc aattggaaac tgaaagctta tcagacccctt   300
```

| | |
|---|---|
| tctggaaatc agcccactgt ttataaactt gaggccccac cctcgagata accagggctg | 360 |
| aaagaggccc gcctggggcc tggagacatg cttgctgcct gccctggcga aggattggca | 420 |
| ggcttgcccg tcacaggacc cccgctggct gactcagggg cgcaggcctc ttgcggggga | 480 |
| gctggcctcc ccgccccac ggccacgggc cgcccttttcc tggcaggaca gcgggatctt | 540 |
| gcagctgtca ggggagggga ggcggggct gatgtcagga gggatacaaa tagtgccgac | 600 |
| ggctgggggc cctgtctccc ctcgccgcat ccactctccg gccggccgcc tgtccgccgc | 660 |
| ctcctccgtg cgcccgccag cctcgcccgc gccgtcaccg tgaggcactg ggcaggtaag | 720 |
| tatcaaagta tcaaggttac aagacaggtt taaggagacc aatagaaact gggcttgtcg | 780 |
| agacagagaa gactcttgcg tttctgatag gcacctattg gtcttactga catccacttt | 840 |
| gcctttctct ccacaggcta gcctcgagaa ttcacgcgtg gtacctctag agtcgaccga | 900 |
| tatcactagt gccaccatgt ggacactggg gagaagggcc gtggctggac tgctggcttc | 960 |
| tccatctcca gcccaggccc agaccctgac cagagtgcct agacctgccg aactggcccc | 1020 |
| tctgtgtggc agaagaggcc tgagaaccga catcgacgcc acctgtaccc ccagaagggc | 1080 |
| cagcagcaat cagcggggcc tgaatcagat ctggaacgtg aagaaacaga gcgtgtacct | 1140 |
| gatgaacctg agaaagagcg gcaccctggg ccaccctgga agcctggatg agacaaccta | 1200 |
| cgagcggctg gccgaggaaa ccctggattc cctggccgag ttcttcgagg acctggccga | 1260 |
| caagccctac accttcgagg attacgacgt gtccttcggc agcggcgtgc tgacagtgaa | 1320 |
| gctgggcgga gatctgggca cctacgtgat caacaagcag accccaaca aacagatctg | 1380 |
| gctgagcagc cccagcagcg gccccaagag atacgattgg accggcaaga actgggtgtt | 1440 |
| cagccacgac ggcgtgtccc tgcatgagct gctggctgcc gagctgacca aggccctgaa | 1500 |
| aacaaagctg gacctgagct ggctggccta gcggcaaa gatgccatcg atatccccag | 1560 |
| ccccgtttta aggacattaa aagctatcag gccaagaccc cagcttcatt atgcagctga | 1620 |
| ggtctgtttt tgttgttgt tgttgtttat ttttttatt cctgcttttg aggacagttg | 1680 |
| ggctatgtgt cacagctctg tagaaagaat gtgttgcctc ctaccttgcc cccaagttct | 1740 |
| gattttaat ttctatggaa gattttttgg attgtcggat ttcctccctc acatgatacc | 1800 |
| ccttatcttt tataatgtct tatgcctata cctgaatata acaacccttta aaaagcaaa | 1860 |
| ataataagaa ggaaaaattc caggagggaa aatgaattgt cttcactctt cattctttga | 1920 |
| aggatttact gcaagaagta catgaagagc agctggtcaa cctgctcact gttctatctc | 1980 |
| caaatgagac acattaaagg gtagcctaca aatgttttca ggcttctttc aaagtgtaag | 2040 |
| cacttctgag ctctttagca ttgaagtgtc gaaagcaact cacacgggaa gatcatttct | 2100 |
| tatttgtgct ctgtgactgc caaggtgtgg cctgcactgg gttgtccagg gagacatgca | 2160 |
| tctagtgctg tttctcccac atattcacat acgtgtctgt gtgtatatat attttttcaa | 2220 |
| tttaaaggtt agtatggaat cagctgctac aagaatgcaa aaaatcttcc aaagacaaga | 2280 |
| aaagaggaaa aaagccgtt ttcatgagct gagtgatgta gcgtaacaaa caaaatcatg | 2340 |
| gagctgagga ggtgccttgt aaacatgaag gggcagataa aggaaggaga tactcatgtt | 2400 |
| gataaagaga gccctggtcc tagacatagt tcagccacaa agtagttgtc cctttgtgga | 2460 |
| caagtttccc aaattccctg gacctctgct tccccatctg ttaaatgaga gaatagagta | 2520 |
| tggttgattc ccagcattca gtggtcctgt caagcaacct aacaggctag ttctaattcc | 2580 |
| ctattgggta gatgagggga tgacaaagaa cagttttttaa gctatatagg aaacattgtt | 2640 |
| attggtgttg ccctatcgtg atttcagttg aattcatgtg aaaataatag ccatccttgg | 2700 |

```
cctggcgcgg tggctcacac ctgtaatccc agcacttttg gaggccaagg tgggtggatc    2760
acctgaggtc aggagttcaa gaccagcctg gccaacatga tgaaacccng tctctactaa    2820
aaatacaaaa aattagccgg gcatgatggc aggtgcctgt aatcccagct acttgggagg    2880
ctgaagcgga agaatcgctt gaacccagag gtggaggttg cagtgagccg agatcgtgcc    2940
attgcactgt aacctgggtg actgagcaaa actctgtctc aaaataataa taacaatata    3000
ataataataa tagccatcct ttattgtacc cttactgggt taatcgtatt ataccacatt    3060
acctcatttt aattttact gacctgcact ttatacaaag caacaagcct ccaggacatt    3120
aaaattcatg caaagttatg ctcatgttat attattttct tacttaaaga aggatttatt    3180
agtggctggg catggtggcg tgcacctgta atcccaggta ctcaggaggc tgagacggga    3240
gaattgcttg accccaggcg gaggaggtta cagtgagtcg agatcgtacc tgagcgacag    3300
agcgagactc cgtctcaaaa aaaaaaaaa ggagggttta ttaatgagaa gtttggtcga    3360
ctagagcggc cgcttcgagc agacatgata agatacattg atgagtttgg acaaaccaca    3420
actagaatgc agtgaaaaaa atgctttatt tgtgaaattt gtgatgctat tgctttattt    3480
gtaaccatta taagctgcaa taaacaagtt aacaacaaca attgcattca ttttatgttt    3540
caggttcagg gggagatgtg gggggttttt taaagcaagt aaaacctcta caaatgtggt    3600
a                                                                    3601

<210> SEQ ID NO 5
<211> LENGTH: 6780
<212> TYPE: DNA
<213> ORGANISM: Artificial Sequence
<220> FEATURE:
<223> OTHER INFORMATION: Synthetic Polynucleotide

<400> SEQUENCE: 5
ctgcaggggg ggggggggg gggttggcca ctccctctct gcgcgctcgc tcgctcactg      60
aggccgggcg accaaaggtc gcccgacgcc cgggctttgc ccggcggcc tcagtgagcg     120 agcgagcgcg cagagaggga gtggccaact ccatcactag ggttcctca gatcttaccc     180 cctgcccccc acagctcctc tcctgtgcct tgtttcccag ccatgcgttc tcctctataa     240
atacccgctc tggtatttgg ggttggcagc tgttgctgcc agggagatgg ttgggttgac     300
atgcggctcc tgacaaaaca caaacccctg gtgtgtgtgg gcgtgggtgg tgtgagtagg     360
gggatgaatc agggagggg cggggaccc aggggcagg agccacacaa agtctgtgcg     420
ggggtgggag cgcacatagc aattggaaac tgaaagctta tcagacccctt tctgaaaatc     480 agcccactgt ttataaactt gaggccccac cctcgagata accagggctg aaagaggccc     540 gcctggggc tggagacatg cttgctgcct gccctggcga aggattggca ggcttgcccg     600
tcacaggacc cccgctggct gactcagggg cgcaggcctc ttgcggggga gctggcctcc     660 ccgccccac ggccacgggc cgcccttcc tggcaggaca gcgggatctt gcagctgtca     720
ggggagggga ggcgggggct gatgtcagga gggatacaaa tagtgccgac ggctgggggc     780
cctgtctccc ctcgccgcat ccactctccg gccggccgcc tgtccgccgc ctcctccgtg     840
cgcccgccag cctcgcccgc gccgtcaccg tgaggcactg gcaggtaag tatcaaagta     900 tcaaggttac aagacaggtt taaggagacc aatagaaact gggcttgtcg agacagagaa     960
gactcttgcg tttctgatag gcaccattg gtcttactga catccacttt gcctttctct    1020
ccacaggcta gcctcgagaa ttcacgcgtg gtacctctag agtcgaccga tatcactagt    1080
```

-continued

```
gccaccatgt ggacactggg gagaagggcc gtggctggac tgctggcttc tccatctcca    1140
gcccaggccc agaccctgac cagagtgcct agacctgccg aactggcccc tctgtgtggc    1200
agaagaggcc tgagaaccga catcgacgcc acctgtaccc ccagaagggc cagcagcaat    1260
cagcggggcc tgaatcagat ctggaacgtg aagaaacaga gcgtgtacct gatgaacctg    1320
agaaagagcg gcaccctggg ccaccctgga agcctggatg agacaaccta cgagcggctg    1380
gccgaggaaa ccctggattc cctggccgag ttcttcgagg acctggccga caagccctac    1440
accttcgagg attacgacgt gtccttcggc agcggcgtgc tgacagtgaa gctgggcgga    1500
gatctgggca cctacgtgat caacaagcag acccccaaca acagatctg gctgagcagc     1560 cccagcagcg gccccaagag atacgattgg accggcaaga actgggtgtt cagccacgac    1620
ggcgtgtccc tgcatgagct gctggctgcc gagctgacca aggccctgaa acaaagctg     1680 gacctgagct ggctggccta cagcggcaaa gatgccatcg atatccccag ccccgtttta    1740
aggacattaa aagctatcag gccaagaccc cagcttcatt atgcagctga ggtctgtttt    1800
ttgttgttgt tgttgtttat ttttttattt cctgcttttg aggacagttg ggctatgtgt    1860
cacagctctg tagaaagaat gtgttgcctc ctaccttgcc cccaagttct gattttaat     1920 ttctatggaa gatttttggg attgtcggat ttcctccctc acatgatacc ccttatcttt    1980
tataatgtct tatgcctata cctgaatata acaacctta aaaaagcaaa ataataagaa     2040
ggaaaaattc caggagggaa aatgaattgt cttcactctt cattctttga aggatttact    2100
gcaagaagta catgaagagc agctggtcaa cctgctcact gttctatctc caaatgagac    2160
acattaaagg gtagcctaca aatgttttca ggcttctttc aaagtgtaag cacttctgag    2220
ctctttagca ttgaagtgtc gaaagcaact cacacgggaa gatcatttct tatttgtgct    2280
ctgtgactgc caaggtgtgg cctgcactgg gttgtccagg gagacatgca tctagtgctg    2340
tttctcccac atattcacat acgtgtctgt gtgtatatat attttttcaa tttaaaggtt    2400
agtatggaat cagctgctac aagaatgcaa aaatcttcc aaagacaaga aaagaggaaa     2460
aaaagccgtt ttcatgagct gagtgatgta gcgtaacaaa caaaatcatg gagctgagga    2520
ggtgccttgt aaacatgaag gggcagataa aggaaggaga tactcatgtt gataaagaga    2580
gccctggtcc tagacatagt tcagccacaa agtagttgtc cctttgtgga caagtttccc    2640
aaattccctg gacctctgct tccccatctg ttaaatgaga gaatagagta tggttgattc    2700
ccagcattca gtggtcctgt caagcaacct aacaggctag ttctaattcc ctattgggta    2760
gatgagggga tgcaaagaa cagttttaa gctatatagg aaacattgtt attggtgttg      2820
ccctatcgtg atttcagttg aattcatgtg aaaataatag ccatccttgg cctggcgcgg    2880
tggctcacac ctgtaatccc agcacttttg gaggccaagg tgggtggatc acctgaggtc    2940
aggagttcaa gaccagcctg gccaacatga tgaaacccg tctctactaa aaatacaaaa     3000
aattagccgg gcatgatggc aggtgcctgt aatcccagct acttgggagg ctgaagcgga    3060
agaatcgctt gaacccagag gtggaggttg cagtgagccg agatcgtgcc attgcactgt    3120
aacctgggtg actgagcaaa actctgtctc aaaataataa taacaatata ataataataa    3180
tagccatcct ttattgtacc cttactgggt taatcgtatt ataccacatt acctcatttt    3240
aatttttact gacctgcact ttatacaaag caacaagcct ccaggacatt aaaattcatg    3300
caaagttatg ctcatgttat attatttttct tacttaaaga aggatttatt agtggctggg    3360
catggtggcg tgcacctgta atcccaggta ctcaggaggc tgacgggga gaattgcttg     3420 accccaggcg gaggaggtta cagtgagtcg agatcgtacc tgagcgacag agcgagactc    3480
```

```
cgtctcaaaa aaaaaaaaaa ggagggttta ttaatgagaa gtttggtcga ctagagcggc    3540
cgcttcgagc agacatgata agatacattg atgagtttgg acaaaccaca actagaatgc    3600
agtgaaaaaa atgctttatt tgtgaaattt gtgatgctat tgctttattt gtaaccatta    3660
taagctgcaa taaacaagtt aacaacaaca attgcattca ttttatgttt caggttcagg    3720
gggagatgtg ggaggttttt taaagcaagt aaaacctcta caaatgtggt aaaatcgata    3780
aggatctagg aaccccctagt gatggagttg gccactccct ctctgcgcgc tcgctcgctc    3840
actgaggccg cccgggcaaa gcccgggcgt cgggcgacct ttggtcgccc ggcctcagtg    3900
agcgagcgag cgcgcagaga gggagtggcc aaccccccccc ccccccccccc tgcagcctgg    3960 cgtaatagcg aagaggcccg caccgatcgc ccttcccaac agttgcgtag cctgaatggc    4020
gaatggcgcg acgcgcctg tagcggcgca ttaagcgcgg cgggtgtggt ggttacgcgc    4080
agcgtgaccg ctacacttgc cagcgcccta gcgcccgctc ctttcgcttt cttcccttcc    4140
tttctcgcca cgttcgccgg ctttccccgt caagctctaa atcggggggct cccttaggg     4200 ttccgattta gtgctttacg gcacctcgac cccaaaaaac ttgattaggg tgatggttca    4260
cgtagtgggc catcgccctg atagacggtt tttcgccctt tgacgttgga gtccacgttc    4320
tttaatagtg gactcttgtt ccaaactgga acaacactca accctatctc ggtctattct    4380
tttgatttat aagggatttt gccgatttcg gcctattggt taaaaaatga gctgatttaa    4440
caaaaattta acgcgaattt taacaaaata ttaacgttta caatttcctg atgcggtatt    4500
ttctccttac gcatctgtgc ggtatttcac accgcatatg gtgcactctc agtacaatct    4560
gctctgatgc cgcatagtta agccagcccc gacacccgcc aacacccgct gacgcgccct    4620
gacgggcttg tctgctcccg gcatccgctt acagacaagc tgtgaccgtc tccgggagct    4680
gcatgtgtca gaggttttca ccgtcatcac cgaaacgcgc gagacgaaag gcctcgtga    4740 tacgcctatt tttataggtt aatgtcatga taataatggt ttcttagacg tcaggtggca    4800
cttttcgggg aaatgtgcgc ggaacccta tttgtttatt tttctaaata cattcaaata    4860
tgtatccgct catgagacaa taaccctgat aaatgcttca ataatattga aaaaggaaga    4920
gtatgagtat tcaacatttc cgtgtcgccc ttattccctt ttttgcggca ttttgccttc    4980 ctgttttttgc tcacccagaa acgctggtga aagtaaaaga tgctgaagat cagttgggtg    5040
cacgagtggg ttacatcgaa ctggatctca acagcggtaa gatccttgag agttttcgcc    5100
ccgaagaacg ttttccaatg atgagcactt taaagttct gctatgtggc gcggtattat    5160
cccgtattga cgccgggcaa gagcaactcg gtcgccgcat acactattct cagaatgact    5220
tggttgagta ctcaccagtc acagaaaagc atcttacgga tggcatgaca gtaagagaat    5280
tatgcagtgc tgccataacc atgagtgata acactgcggc caacttactt ctgacaacga    5340
tcggaggacc gaaggagcta accgcttttt tgcacaacat ggggatcat gtaactcgcc    5400 ttgatcgttg ggaaccggag ctgaatgaag ccataccaaa cgacgagcgt gacaccacga    5460
tgcctgtagc aatggcaaca acgttgcgca aactattaac tggcgaacta cttactctag    5520
cttcccggca caattaata gactggatgg aggcggataa agttgcagga ccacttctgc    5580
gctcggccct tccggctggc tggtttattg ctgataaatc tggagccggt gagcgtgggt    5640
ctcgcggtat cattgcagca ctggggccag atggtaagcc ctcccgtatc gtagttatct    5700
acacgacggg gagtcaggca actatggatg aacgaaatag acagatcgct gagataggtg    5760
cctcactgat taagcattgg taactgtcag accaagttta ctcatatata ctttagattg    5820
```

```
atttaaaact tcatttttaa tttaaaagga tctaggtgaa gatccttttt gataatctca   5880
tgaccaaaat cccttaacgt gagttttcgt tccactgagc gtcagacccc gtagaaaaga   5940
tcaaaggatc ttcttgagat cctttttttc tgcgcgtaat ctgctgcttg caaacaaaaa   6000
aaccaccgct accagcggtg gtttgtttgc cggatcaaga gctaccaact cttttttccga  6060 aggtaactgg cttcagcaga gcgcagatac caaatactgt ccttctagtg tagccgtagt   6120
taggccacca cttcaagaac tctgtagcac cgcctacata cctcgctctg ctaatcctgt   6180
taccagtggc tgctgccagt ggcgataagt cgtgtcttac cgggttggac tcaagacgat   6240
agttaccgga taaggcgcag cggtcgggct gaacggggg ttcgtgcaca cagcccagct    6300
tggagcgaac gacctacacc gaactgagat acctacagcg tgagcattga aaagcgcca    6360 cgcttcccga agggagaaag gcggacaggt atccggtaag cggcagggtc ggaacaggag   6420
agcgcacgag ggagcttcca gggggaaacg cctggtatct ttatagtcct gtcgggtttc   6480
gccacctctg acttgagcgt cgatttttgt gatgctcgtc aggggggcgg agcctatgga   6540
aaaacgccag caacgcggcc ttttacggtt cctggccctt tgctggcct tttgctcaca    6600 tgttctttcc tgcgttatcc cctgattctg tggataaccg tattaccgcc tttgagtgag   6660
ctgataccgc tcgccgcagc cgaacgaccg agcgcagcga gtcagtgagc gaggaagcgg   6720
aagagcgccc aatacgcaaa ccgcctctcc ccgcgcgttg gccgattcat taatgcaggg   6780
```

\<210\> SEQ ID NO 6  
\<211\> LENGTH: 315  
\<212\> TYPE: PRT  
\<213\> ORGANISM: Homo sapiens

\<400\> SEQUENCE: 6

```
Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Phe Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Trp Leu Ala Tyr Ser Gly Lys
        195                 200                 205
```

Asp Ala Ile Asp Ile Pro Ser Pro Val Leu Arg Thr Leu Lys Ala Ile
210                 215                 220

Arg Pro Arg Pro Gln Leu His Tyr Ala Ala Glu Val Cys Phe Leu Leu
225                 230                 235                 240

Leu Leu Leu Phe Ile Phe Phe Ile Pro Ala Phe Glu Asp Ser Trp Ala
            245                 250                 255

Met Cys His Ser Ser Val Glu Arg Met Cys Cys Leu Leu Pro Cys Pro
            260                 265                 270

Gln Val Leu Ile Phe Asn Phe Tyr Gly Arg Phe Gly Leu Ser Asp
        275                 280                 285

Phe Leu Pro His Met Ile Pro Leu Ile Phe Tyr Asn Val Leu Cys Leu
290                 295                 300

Tyr Leu Asn Ile Thr Thr Phe Lys Lys Ala Lys
305                 310                 315

<210> SEQ ID NO 7
<211> LENGTH: 1769
<212> TYPE: DNA
<213> ORGANISM: Artificial Sequence
<220> FEATURE:
<223> OTHER INFORMATION: Synthetic Polynucleotide

<400> SEQUENCE: 7
ctagatctga attcggtacc ctagttatta atagtaatca attacgggt cattagttca      60 tagcccatat atggagttcc gcgttacata acttacggta aatggcccgc ctggctgacc    120
gcccaacgac cccgcccat tgacgtcaat aatgacgtat gttcccatag taacgccaat    180
agggactttc cattgacgtc aatgggtgga ctatttacgg taaactgccc acttggcagt    240
acatcaagtg tatcatatgc caagtacgcc ccctattgac gtcaatgacg gtaaatggcc    300
cgcctggcat tatgcccagt acatgacctt atgggacttt cctacttggc agtacatcta    360
cgtattagtc atcgctatta ccatggtcga ggtgagcccc acgttctgct tcactctccc    420
catctccccc ccctccccac ccccaatttt gtatttattt attttttaat tattttgtgc    480
agcgatgggg gcgggggggg ggggggggcg cgcgccaggc ggggcgggc ggggcgaggg    540 gcggggcggg gcgaggcgga gaggtgcggc ggcagccaat cagagcggcg cgctccgaaa    600
gtttcctttt atggcgaggc ggcggcggc gcggccctat aaaaagcgaa gcgcgcggcg    660
ggcgggagtc gctgcgacgc tgccttcgcc ccgtgccccg ctccgccgcc gcctcgcgcc    720 gcccgcccg gctctgactg accgcgttac tcccacaggt gagcgggcgg gacggcccctt    780 ctcctccggg ctgtaattag cgcttggttt aatgacggct tgtttctttt ctgtggctgc    840
gtgaaagcct tgagggct cggagggcc ctttgtgcgg gggagcgg ctcgggggt    900 gcgtgcgtgt gtgtgtgcgt ggggagcgcc gcgtgcggcc cgcgctgccc ggcggctgtg    960
agcgctgcgg gcgcggcgcg gggctttgtg cgctccgcag tgtgcgcgag gggagcgcgg   1020 ccggggggcgg tgccccgcgg tgcgggggg gctgcgaggg gaacaaaggc tgcgtgcggg   1080
gtgtgtgcgt gggggggtga gcaggggtg tgggcgcggc ggtcgggctg taaccccccc   1140
ctgcaccccc ctccccgagt tgctgagcac ggcccggctt cgggtgcggg gctccgtacg   1200
gggcgtggcg cggggctcgc cgtgccggc ggggggtggc ggcaggtggg ggtgccgggc   1260 ggggcgggc cgcctcgggc cggggagggc tcggggagg ggcgcggcgg ccccggagc   1320 gccggcggct gtcgaggcgc ggcgagccgc agccattgcc ttttatggta atcgtgcgag   1380
agggcgcagg gacttccttt gtcccaaatc tgtgcggagc cgaaatctgg gaggcgccgc   1440

| | |
|---|---|
| cgcacccct ctagcgggcg cggggcgaag cggtgcggcg ccggcaggaa ggaaatgggc | 1500 |
| ggggagggcc ttcgtgcgtc gccgcgccgc cgtccccttc tccctctcca gcctcggggc | 1560 |
| tgtccgcggg gggacggctg ccttcggggg ggacggggca gggcggggtt cggcttctgg | 1620 |
| cgtgtgaccg gcggctctag agcctctgct aaccatgttc atgccttctt cttttttccta | 1680 |
| cagctcctgg gcaacgtgct ggttattgtg ctgtctcatc attttggcaa agaattcctc | 1740 |
| gaagatccga aggggttcaa gcttaaaaa | 1769 |

<210> SEQ ID NO 8
<211> LENGTH: 1220
<212> TYPE: DNA
<213> ORGANISM: Homo sapiens

<400> SEQUENCE: 8

| | |
|---|---|
| aagaaaactt tcacaatttg catcccttg taatatgtaa cagaaataaa attctctttt | 60 |
| aaaatctatc aacaataggc aaggcacggt ggctcacgcc tgtcgtctca gcactttgtg | 120 |
| aggcccaggc gggcagatcg tttgagccta gaagttcaag accaccctgg gcaacatagc | 180 |
| gaaacccct ttctacaaaa aatacaaaaa ctagctgggt gtggtggtgc acacctgtag | 240 |
| tcccagctac ttggaaggct gaaatgggaa gactgcttga gccgggagg gagaagttgc | 300 |
| agtaagccag gaccacacca ctgcactcca gcctgggcaa cagagtgaga ctctgtctca | 360 |
| aacaaacaaa taaatgaggc gggtggatca cgaggtcagt agatcgagac catcctggct | 420 |
| aacacggtga aacccgtctc tactaaaaaa aaaaaaaaat acaaaaaatt agccaggcat | 480 |
| ggtggcgggc gcctgtagtc ccagttactc gggaggctga gcaggagaa tggcgtgaaa | 540 |
| ccgggaggca gagcttgcag tgagccgaga tcgcaccact gcctccagc ctgggcgaca | 600 |
| gagcgagact ccgtctcaat caatcaatca atcaataaaa tctattaaca atatttattg | 660 |
| tgcacttaac aggaacatgc cctgtccaaa aaaacttta cagggcttaa ctcattttat | 720 |
| ccttaccaca atcctatgaa gtaggaactt ttataaaacg cattttataa acaaggcaca | 780 |
| gagaggttaa ttaacttgcc ctctggtcac acagctagga agtgggcaga gtacagattt | 840 |
| acacaaggca tccgtctcct ggccccacat acccaactgc tgtaaaccca taccggcggc | 900 |
| caagcagcct caatttgtgc atgcacccac ttcccagcaa gacagcagct cccaagttcc | 960 |
| tcctgtttag aattttagaa gcggcgggcc accaggctgc agtctccctt gggtcagggg | 1020 |
| tcctggttgc actccgtgct ttgcacaaag caggctctcc atttttgtta aatgcacgaa | 1080 |
| tagtgctaag ctgggaagtt cttcctgagg tctaacctct agctgctccc ccacagaaga | 1140 |
| gtgcctgcgg ccagtggcca ccaggggtcg ccgcagcacc cagcgctgga gggcggagcg | 1200 |
| ggcggcagac ccggagcagc | 1220 |

<210> SEQ ID NO 9
<211> LENGTH: 2457
<212> TYPE: DNA
<213> ORGANISM: Homo sapiens

<400> SEQUENCE: 9

| | |
|---|---|
| actagtgcca ccatgtggac actggggaga agggccgtgg ctggactgct ggcttctcca | 60 |
| tctccagccc aggcccagac cctgaccaga gtgcctagac ctgccgaact ggcccctctg | 120 |
| tgtggcagaa gaggcctgag aaccgacatc gacgccacct gtaccccag aagggccagc | 180 |
| agcaatcagc ggggcctgaa tcagatctgg aacgtgaaga acagagcgt gtacctgatg | 240 |
| aacctgagaa agagcggcac cctgggccac cctggaagcc tggatgagac aacctacgag | 300 |

```
cggctggccg aggaaaccct ggattccctg gccgagttct tcgaggacct ggccgacaag      360
ccctacacct tcgaggatta cgacgtgtcc ttcggcagcg cgtgctgac agtgaagctg       420 ggcggagatc tgggcaccta cgtgatcaac aagcagaccc ccaacaaaca gatctggctg      480
agcagcccca gcagcggccc caagagatac gattggaccg gcaagaactg ggtgttcagc     540
cacgacggcg tgtccctgca tgagctgctg gctgccgagc tgaccaaggc cctgaaaaca      600
aagctggacc tgagctggct ggcctacagc ggcaaagatg ccatcgatat ccccagcccc      660
gttttaagga cattaaaagc tatcaggcca gaccccagc ttcattatgc agctgaggtc       720
tgttttttgt tgttgttgtt gtttattttt tttattcctg cttttgagga cagttgggct      780
atgtgtcaca gctctgtaga agaatgtgt tgcctcctac cttgccccca agttctgatt       840
tttaatttct atggaagatt ttttggattg tcggatttcc tccctcacat gatccccttt       900
atcttttata tgtcttatg cctatacctg aatataacaa cctttaaaaa agcaaaataa       960
taagaaggaa aaattccagg agggaaaatg aattgtcttc actcttcatt ctttgaagga     1020
tttactgcaa gaagtacatg aagagcagct ggtcaacctg ctcactgttc tatctccaaa     1080
tgagacacat taaagggtag cctacaaatg ttttcaggct tctttcaaag tgtaagcact      1140
tctgagctct ttagcattga agtgtcgaaa gcaactcaca cgggaagatc atttcttatt      1200
tgtgctctgt gactgccaag gtgtggcctg cactgggttg tccagggaga catgcatcta     1260
gtgctgtttc tcccacatat tcacatacgt gtctgtgtgt atatatattt tttcaattta     1320
aaggttagta tggaatcagc tgctacaaga atgcaaaaaa tcttccaaag acaagaaaag     1380
aggaaaaaaa gccgttttca tgagctgagt gatgtagcgt aacaaacaaa atcatggagc     1440
tgaggaggtg ccttgtaaac atgaaggggc agataaagga aggagatact catgttgata      1500
aagagagccc tggtcctaga catagttcag ccacaaagta gttgtccctt tgtggacaag     1560
tttcccaaat tccctggacc tctgcttccc catctgttaa atgagagaat agagtatggt     1620
tgattcccag cattcagtgg tcctgtcaag caacctaaca ggctagttct aattccctat     1680
tgggtagatg agggggatgac aaagaacagt ttttaagcta tataggaaac attgttattg     1740
gtgttgccct atcgtgattt cagttgaatt catgtgaaaa taatagccat ccttggcctg     1800
gcgcggtggc tcacacctgt aatcccagca cttttggagg ccaaggtggg tggatcacct     1860
gaggtcagga gttcaagacc agcctggcca acatgatgaa accccgtctc tactaaaaat      1920
acaaaaaatt agccgggcat gatggcaggt gcctgtaatc ccagctactt gggaggctga     1980
agcggaagaa tcgcttgaac ccagaggtgg aggttgcagt gagccgagat cgtgccattg     2040
cactgtaacc tgggtgactg agcaaaactc tgtctcaaaa taataataac aatataataa     2100
taataatagc catcctttat tgtacccta ctgggttaat cgtattatac cacattacct        2160
cattttaatt tttactgacc tgcactttat acaaagcaac aagcctccag gacattaaaa      2220
ttcatgcaaa gttatgctca tgttatatta ttttcttact aaagaagga tttattagtg        2280 gctgggcatg gtggcgtgca cctgtaatcc caggtactca ggaggctgag acgggagaat     2340
tgcttgaccc caggcggagg aggttacagt gagtcgagat cgtacctgag cgacagagcg     2400
agactccgtc tcaaaaaaaa aaaaaaggag ggtttattaa tgagaagttt ggtcgac        2457
```

<210> SEQ ID NO 10
<211> LENGTH: 6780
<212> TYPE: DNA
<213> ORGANISM: Artificial Sequence
<220> FEATURE:

<223> OTHER INFORMATION: Synthetic Polynucleotide

<400> SEQUENCE: 10

```
ctgcaggggg ggggggggggg gggttggcca ctccctctct gcgcgctcgc tcgctcactg     60
aggccgggcg accaaaggtc gcccgacgcc cgggctttgc ccgggcggcc tcagtgagcg    120
agcgagcgcg cagagaggga gtggccaact ccatcactag gggttcctca gatcttaccc    180
cctgccccccc acagctcctc tcctgtgcct tgtttcccag ccatgcgttc tcctctataa    240
atacccgctc tggtatttgg ggttggcagc tgttgctgcc agggagatgg ttgggttgac    300
atgcggctcc tgacaaaaca caaacccctg gtgtgtgtgg gcgtgggtgg tgtgagtagg    360
gggatgaatc agggaggggg cggggggaccc aggggggcagg agccacacaa agtctgtgcg    420
ggggtgggag cgcacatagc aattggaaac tgaaagctta tcagacccct tctggaaatc    480
agcccactgt ttataaactt gaggccccac cctcgagata accagggctg aaagaggccc    540
gcctggggggc tggagacatg cttgctgcct gccctggcga aggattggca ggcttgcccg    600
tcacaggacc cccgctggct gactcagggg cgcaggcctc ttgcggggga gctggcctcc    660
ccgcccccac ggccacgggc cgcccttttcc tggcaggaca cgggatcttt gcagctgtca    720
ggggagggga ggcggggggct gatgtcagga gggatacaaa tagtgccgac ggctgggggc    780
cctgtctccc ctcgccgcat ccactctccg gccggccgcc tgtccgccgc ctcctccgtg    840
cgcccgccag cctcgcccgc gccgtcaccg tgaggcactg gcaggtaag tatcaaagta    900
tcaaggttac aagacaggtt taaggagacc aatagaaact gggcttgtcg agacagagaa    960
gactcttgcg tttctgatag gcacctattg gtcttactga catccacttt gcctttctct   1020
ccacaggcta gcctcgagaa ttcacgcgtg gtacctctag agtcgaccga tatcactagt   1080
gccaccatgt ggacactggg gagaagggcc gtggctggac tgctggcttc tccatctcca   1140
gcccaggccc agaccctgac cagagtgcct agacctgccg aactggcccc tctgtgtggc   1200
agaagaggcc tgaaaccgga catcgacgcc acctgtaccc ccagaagggc cagcagcaat   1260
cagcggggcc tgaatcagat ctggaacgtg aagaaacaga gcgtgtacct gatgaacctg   1320
agaaagagcg gcacccctgggg ccaccctgga agcctggatg agacaaccta cgagcggctg   1380
gccgaggaaa ccctggattc cctggccgag ttcttcgagg acctggccga caagccctac   1440
accttcgagg attacgacgt gtccttcggc agcggcgtgc tgacagtgaa gctgggcgga   1500
gatctgggca cctacgtgat caacaagcag accccccaaca aacagatctg gctgagcagc   1560
cccagcagcg gccccaagag atacgattgg accggcaaga ctgggtgtt cagccacgac   1620
ggcgtgtccc tgcatgagct gctggctgcc gagctgacca aggccctgaa acaaagctg   1680
gacctgagct ggctggccta cagcggcaaa gatgccatcg atatccccag ccccgttttta   1740
aggacattaa aagctatcag gccaagaccc cagcttcatt atgcagctga ggtctgtttt   1800
ttgttgttgt tgttgtttat ttttttttatt cctgcttttg aggacagttg ggctatgtgt   1860
cacagctctg tagaaagaat gtgttgcctc ctaccttgcc cccaagttct gatttttaat   1920
ttctatggaa gatttttttgg attgtcggat ttcctccctc acatgatacc ccttatcttt   1980
tataatgtct tatgcctata cctgaatata acaacctta aaaaagcaaa ataataagaa   2040
ggaaaaattc caggagggaa aatgaattgt cttcactctt cattctttga aggatttact   2100
gcaagaagta catgaagagc agctggtcaa cctgctcact gttctatctc caaatgagac   2160
acattaaagg gtagcctaca aatgttttca ggcttctttc aaagtgtaag cacttctgag   2220
ctctttagca ttgaagtgtc gaaagcaact cacacgggaa gatcatttct tatttgtgct   2280
```

```
ctgtgactgc caaggtgtgg cctgcactgg gttgtccagg gagacatgca tctagtgctg    2340
tttctcccac atattcacat acgtgtctgt gtgtatatat attttttcaa tttaaaggtt    2400
agtatggaat cagctgctac aagaatgcaa aaatcttcc  aaagacaaga aaagaggaaa    2460
aaaagccgtt ttcatgagct gagtgatgta gcgtaacaaa caaatcatg  gagctgagga    2520 ggtgccttgt aaacatgaag gggcagataa aggaaggaga tactcatgtt gataaagaga    2580
gccctggtcc tagacatagt tcagccacaa agtagttgtc cctttgtgga caagtttccc    2640
aaattccctg gacctctgct tccccatctg ttaaatgaga gaatagagta tggttgattc    2700
ccagcattca gtggtcctgt caagcaacct aacaggctag ttctaattcc ctattgggta    2760
gatgagggga tgacaaagaa cagttttaa  gctatatagg aaacattgtt attggtgttg    2820
ccctatcgtg atttcagttg aattcatgtg aaaataatag ccatccttgg cctggcgcgg    2880
tggctcacac ctgtaatccc agcacttttg gaggccaagg tgggtggatc acctgaggtc    2940
aggagttcaa gaccagcctg gccaacatga tgaaaccccg tctctactaa aaatacaaaa    3000
aattagccgg gcatgatggc aggtgcctgt aatcccagct acttgggagg ctgaagcgga    3060
agaatcgctt gaacccagag gtggaggttg cagtgagccg agatcgtgcc attgcactgt    3120
aacctgggtg actgagcaaa actctgtctc aaaataataa taacaatata ataataataa    3180
tagccatcct ttattgtacc cttactgggt taatcgtatt ataccacatt acctcatttt    3240
aatttttact gacctgcact ttatacaaag caacaagcct ccaggacatt aaaattcatg    3300
caaagttatg ctcatgttat attattttct tacttaaaga aggatttatt agtggctggg    3360
catggtggcg tgcacctgta atcccaggta ctcaggaggc tgagacggga gaattgcttg    3420
accccaggcg gaggaggtta cagtgagtcg agatcgtacc tgagcgacag agcgagactc    3480
cgtctcaaaa aaaaaaaaaa ggagggttta ttaatgagaa gtttggtcga ctagagcggc    3540
cgcttcgagc agacatgata agatacattg atgagtttgg acaaccaca  actgaatgc    3600 agtgaaaaaa atgctttatt tgtgaaattt gtgatgctat tgctttattt gtaaccatta    3660
taagctgcaa taaacaagtt aacaacaaca attgcattca ttttatgttt caggttcagg    3720
gggagatgtg ggaggttttt taaagcaagt aaaacctcta caaatgtggt aaaatcgata    3780
aggatctagg aaccccccct agaggatgct gccactccct ctctgcgcgc tcgctcgctc    3840
actgaggccg cccgggcaaa gcccgggcgt cgggcgacct ttggtcgccc ggcctcagtg    3900
agcgagcgag cgcgcagaga gggagtggcc aacccccccc cccccccccc tgcagcctgg    3960
cgtaatagcg aagaggcccg caccgatcgc ccttcccaac agttgcgtag cctgaatggc    4020
gaatggcgcg acgcgccctg tagcggcgca ttaagcgcgg cgggtgtggt ggttacgcgc    4080
agcgtgaccg ctacacttgc cagcgcccta gcgcccgctc ctttcgcttt cttcccttcc    4140
tttctcgcca cgttcgccgg ctttccccgt caagctctaa atcgggggct ccctttaggg    4200
ttccgattta gtgctttacg gcacctcgac cccaaaaaac ttgattaggg tgatggttca    4260
cgtagtgggc catcgccctg atagacggtt tttcgccctt tgacgttgga gtccacgttc    4320
tttaatagtg gactcttgtt ccaaactgga acaacactca accctatctc ggtctattct    4380
tttgatttat aagggatttt gccgatttcg gcctattggt taaaaaatga ctgatttaa    4440 caaaatttta acgcgaattt taacaaaata ttaacgttta caatttcctg atgcggtatt    4500
ttctccttac gcatctgtgc ggtatttcac accgcatatg gtgcactctc agtacaatct    4560
gctctgatgc cgcatagtta agccagcccc gacacccgcc aacacccgct gacgcgccct    4620
```

```
gacgggcttg tctgctcccg gcatccgctt acagacaagc tgtgaccgtc tccgggagct    4680
gcatgtgtca gaggttttca ccgtcatcac cgaaacgcgc gagacgaaag ggcctcgtga    4740
tacgcctatt tttataggtt aatgtcatga taataatggt ttcttagacg tcaggtggca    4800
cttttcgggg aaatgtgcgc ggaaccccta tttgtttatt tttctaaata cattcaaata    4860
tgtatccgct catgagacaa taaccctgat aaatgcttca ataatattga aaaggaaga    4920 gtatgagtat tcaacatttc cgtgtcgccc ttattccctt ttttgcggca ttttgccttc    4980 ctgttttgc tcacccagaa acgctggtga agtaaaaga tgctgaagat cagttgggtg    5040
cacgagtggg ttacatcgaa ctggatctca acagcggtaa gatccttgag agttttcgcc    5100
ccgaagaacg ttttccaatg atgagcactt ttaaagttct gctatgtggc gcggtattat    5160
cccgtattga cgccgggcaa gagcaactcg gtcgccgcat acactattct cagaatgact    5220
tggttgagta ctcaccagtc acagaaaagc atcttacgga tggcatgaca gtaagagaat    5280
tatgcagtgc tgccataacc atgagtgata acactgcggc caacttactt ctgacaacga    5340
tcggaggacc gaaggagcta accgcttttt tgcacaacat gggggatcat gtaactcgcc    5400
ttgatcgttg ggaaccggag ctgaatgaag ccataccaaa cgacgagcgt gacaccacga    5460
tgcctgtagc aatggcaaca acgttgcgca aactattaac tggcgaacta cttactctag    5520
cttcccggca acaattaata gactggatgg aggcggataa agttgcagga ccacttctgc    5580
gctcggccct tccggctggc tggtttattg ctgataaatc tggagccggt gagcgtgggt    5640
ctcgcggtat cattgcagca ctggggccag atggtaagcc ctcccgtatc gtagttatct    5700
acacgacggg gagtcaggca actatggatg aacgaaatag acagatcgct gagataggtg    5760
cctcactgat taagcattgg taactgtcag accaagttta ctcatatata ctttagattg    5820
atttaaaact tcattttaa tttaaaagga tctaggtgaa gatccttttt gataatctca    5880
tgaccaaaat cccttaacgt gagttttcgt tccactgagc gtcagacccc gtagaaaaga    5940
tcaaaggatc ttcttgagat ccttttttc tgcgcgtaat ctgctgcttg caaacaaaaa    6000
aaccaccgct accagcggtg gtttgtttgc cggatcaaga gctaccaact ctttttccga    6060
aggtaactgg cttcagcaga gcgcagatac caaatactgt ccttctagtg tagccgtagt    6120
taggccacca cttcaagaac tctgtagcac cgcctacata cctcgctctg ctaatcctgt    6180
taccagtggc tgctgccagt ggcgataagt cgtgtcttac cgggttggac tcaagacgat    6240
agttaccgga taaggcgcag cggtcgggct gaacggggg ttcgtgcaca cagcccagct    6300
tggagcgaac gacctacacc gaactgagat acctacagcg tgagcattga aaagcgcca    6360 cgcttcccga agggagaaag gcggacaggt atccggtaag cggcagggtc ggaacaggag    6420
agcgcacgag ggagcttcca gggggaaacg cctggtatct ttatagtcct gtcgggtttc    6480
gccacctctg acttgagcgt cgatttttgt gatgctcgtc aggggggcgg agcctatgga    6540
aaaacgccag caacgcggcc tttttacggt tcctggcctt ttgctggcct tttgctcaca    6600
tgttctttcc tgcgttatcc cctgattctg tggataaccg tattaccgcc tttgagtgag    6660
ctgataccgc tcgccgcagc cgaacgaccg agcgcagcga gtcagtgagc gaggaagcgg    6720
aagagcgccc aatacgcaaa ccgcctctcc ccgcgcgttg gccgattcat taatgcaggg    6780
```

<210> SEQ ID NO 11
<211> LENGTH: 315
<212> TYPE: PRT
<213> ORGANISM: Artificial Sequence
<220> FEATURE:
<223> OTHER INFORMATION: Synthetic Polypeptide

```
<400> SEQUENCE: 11

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
            85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Phe Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Trp Leu Ala Tyr Ser Gly Lys
            195                 200                 205

Asp Ala Ile Asp Ile Pro Ser Pro Val Leu Arg Thr Leu Lys Ala Ile
            210                 215                 220

Arg Pro Arg Pro Gln Leu His Tyr Ala Ala Glu Val Cys Phe Leu Leu
225                 230                 235                 240

Leu Leu Leu Phe Ile Phe Phe Ile Pro Ala Phe Glu Asp Ser Trp Ala
                245                 250                 255

Met Cys His Ser Ser Val Glu Arg Met Cys Cys Leu Leu Pro Cys Pro
            260                 265                 270

Gln Val Leu Ile Phe Asn Phe Tyr Gly Arg Phe Phe Gly Leu Ser Asp
            275                 280                 285

Phe Leu Pro His Met Ile Pro Leu Ile Phe Tyr Asn Val Leu Cys Leu
            290                 295                 300

Tyr Leu Asn Ile Thr Thr Phe Lys Lys Ala Lys
305                 310                 315
```